United States Patent [19]

Pittman et al.

[11] Patent Number: 5,563,045
[45] Date of Patent: Oct. 8, 1996

[54] CHIMERIC PROCOAGULANT PROTEINS

[75] Inventors: Debra Pittman, Windham, N.H.;
Alnawaz Rehemtulla, Ann Arbor,
Mich.; John M. Wozney, Hudson;
Randal J. Kaufman, Boston, both of
Mass.

[73] Assignee: Genetics Institute, Inc., Cambridge, Mass.

[21] Appl. No.: 121,202

[22] Filed: Sep. 14, 1993

Related U.S. Application Data

[63] Continuation-in-part of Ser. No. 976,086, Nov. 13, 1992, abandoned.
[51] Int. Cl.⁶ ............... C12P 21/02; A61K 38/37; C12N 15/70; C12N 15/12
[52] U.S. Cl. ............... 435/69.6; 435/320.1; 435/252.3; 435/252.33; 435/240.2; 514/12; 536/23.4; 536/23.5
[58] Field of Search ............... 435/69.1, 69.6, 435/252.3; 514/2, 12; 536/23.4, 23.5, 320.1, 252.33, 240.2

[56] References Cited

U.S. PATENT DOCUMENTS 5,364,771 11/1994 Lolar et al. ............... 435/69.1

FOREIGN PATENT DOCUMENTS

WO93/20093 10/1993 WIPO .

OTHER PUBLICATIONS

Lee et al. Science 239 1288 (1988)
Ferraiolo et al Protein Pharmokinetics and Metabolism Chapter 1 pp. 1–33, Plenum Press N.Y. (1992).
Konrad, Biological Barriers to Protein Delivery, Chapter 14, pp. 409–437 Plenum Press N.Y. (1993).
Kaufman, Nature 342:207–208 (1989).
Lollar, et al., J. Biol Chem. 266:12481–12486 (1991).
Fay, et al., J. Biol. Chem. 266:8957–8962 (1991).
Pittman, et al., Blood 79:389–397 (1992).
Toole, et al., Nature 312:342–347 (1984).
Wood, et al., Nature 312:330–336 (1984).
Vehar, et al., Nature 312:337–342 (1984).
Church, et al., Proc. Natl. Acad. Sci. U.S.A. 81:6934–6937 (1984).
Toole, et al., Nature 312:342–347 (1984).
Toole, et al., Proc. Natl. Acad. Sci. U.S.A. 83:5939–5942 (1986).

Primary Examiner—Charles L. Patterson, Jr.
Attorney, Agent, or Firm—M. C. Meinert

[57] ABSTRACT

Provided are porcine factor VIII nucleotide sequences and hybrid sequences encoding human/porcine chimeric factor VIII-type procoagulant proteins. DNAs encoding such chimeric factor VIII-type procoagulant proteins, pharmaceutical compositions containing such chimeric factor VIII-type procoagulant proteins, and methods of treating hemophilia using such chimeric factor VIII-type procoagulant proteins are also provided.

26 Claims, 2 Drawing Sheets

Figure 1

```
  1 FAVFDEGKSWHSARNDSWTRAMDPAPARAQPAMHTVNGYVNRSLPGLIGC  50 pVIII
    ||||||||||||.  .:|:  ...|:|.|||  |  ||||||||||||||||||
199 FAVFDEGKSWHSETKNSLMQDRDAASARAWPKMHTVNGYVNRSLPGLIGC 248 hVIII

51 HKKSVYWHVIGMGTSPEVHSIFLEGHTFLVRHHRQASLEISPLTFLTAQT 100
    |:|||||||||||.|||||||||||||||:|||||||||||:|||||||
249 HRKSVYWHVIGMGTTPEVHSIFLEGHTFLVRNHRQASLEISPITFLTAQT 298

101 FLMDLGQFLLFCHISSHHHGGMEAHVRVESCAEEPQLRRKADEE.EDYDD 149
    :||||||||||||||:|:|||.|:|:||:||||.|.:||  |||||
299 LLMDLGQFLLFCHISSHQHDGMEAYVKVDSCPEEPQLRMKNNEEAEDYDD 348

150 NLYDSDMDVVRLDGDDVSPFIQIRSVAKKHPKTWVHYISAEEEDWDYAPA 199
    :|  ||:||||:|:|:  ..|||||||||||||||||.||||||||||
349 DLTDSEMDVVRFDDDNSPSFIQIRSVAKKHPKTWVHYIAAEEEDWDYAPL 398

200 VPSPSDRSYKSLYLNSGPQRIGRKYKKARFVAYTDVTFKTRKAIPYESGI 249
    |  .|.||||| |||.|||||||||||.||:||||  |||||.|..||||
399 VLAPDDRSYKSQYLNNGPQRIGRKYKKVRFMAYTDETFKTREAIQHESGI 448

250 LGPLLYGEVGDTLLIIFKNKASRPYNIYPHGITDVSALHPGRLLKGWKHL 299
    ||||||||||||||||||.|||||||||||||||..:|..  ||  |||
449 LGPLLYGEVGDTLLIIFKNQASRPYNIYPHGITDVRPLYSRRLPKGVKHL 498

300 KDMPILPGETFKYKWTVTVEDGPTKSDPRCLTRYYSSSINLEKDLASGLI 349
    ||:|||||.||||||||||||||||||||||||||||  :|:|:|||||
449 KDFPILPGEIFKYKWTVTVEDGPTKSDPRCLTRYYSSFVNMERDLASGLI 548

350 GPLLICYKESVDQRGNQMMSDKRNVILFSVFDENQSWYLAENIQRFLPNP 399
    ||||||||||||||||||:|||||||||||||||.||||.||||||||||
549 GPLLICYKESVDQRGNQIMSDKRNVILFSVFDENRSWYLTENIQRFLPNP 598

400 DGLQPQDPEFQASNIMHSINGYVFDSLQLSVCLHEVAYWYILSVGAQTDF 449
    .|:|  :|||||||||||||||||||||||||||||||||||||:||||||
599 AGVQLEDPEFQASNIMHSINGYVFDSLQLSVCLHEVAYWYILSIGAQTDF 648

450 LSVFFSGYTFKHKMVYEDTLTLFPFSGETVFMSMENPGLWVLGCHNSDLR 499
    |||||||||||||||||||||||||||||||||||||||:|||||||:|
649 LSVFFSGYTFKHKMVYEDTLTLFPFSGETVFMSMENPGLWILGCHNSDFR 698

500 NRGMTALLKVYSCDRDIGDYYDNTYEDIPGFLLSGKNVIEPR 541
    ||||||||||  |||::.||||::.|||||.::|||  .|.||||
699 NRGMTALLKVSSCDKNTGDYYEDSYEDISAYLLSKNNAIEPR 740
```

FIGURE 2

| A1 | | A2 | | B | | A3 | C1 | C2 |
|----|--|----|--|---|--|----|----|----|
| 1  336 | 372 | | 700 | 740 | 1689 | | 2020  2173 | 2332 |

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 7056 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..7053

( x i ) SEQUENCE DESCRIPTION: SEQ ID NO:1:

```
ATG  CAA  ATA  GAG  CTC  TCC  ACC  TGC  TTC  TTT  CTG  TGC  CTT  TTG  CGA  TTC        48
Met  Gln  Ile  Glu  Leu  Ser  Thr  Cys  Phe  Phe  Leu  Cys  Leu  Leu  Arg  Phe
  1              5                        10                       15

TGC  TTT  AGT  GCC  ACC  AGA  AGA  TAC  TAC  CTG  GGT  GCA  GTG  GAA  CTG  TCA        96
Cys  Phe  Ser  Ala  Thr  Arg  Arg  Tyr  Tyr  Leu  Gly  Ala  Val  Glu  Leu  Ser
            20                       25                       30
```

| | | | | | | | | | | | | | | | | |
|---|---|---|---|---|---|---|---|---|---|---|---|---|---|---|---|---|
| TGG | GAC | TAT | ATG | CAA | AGT | GAT | CTC | GGT | GAG | CTG | CCT | GTG | GAC | GCA | AGA | 144 |
| Trp | Asp | Tyr 35 | Met | Gln | Ser | Asp | Leu 40 | Gly | Glu | Leu | Pro | Val 45 | Asp | Ala | Arg | |
| TTT | CCT | CCT | AGA | GTG | CCA | AAA | TCT | TTT | CCA | TTC | AAC | ACC | TCA | GTC | GTG | 192 |
| Phe | Pro 50 | Pro | Arg | Val | Pro | Lys 55 | Ser | Phe | Pro | Phe | Asn 60 | Thr | Ser | Val | Val | |
| TAC | AAA | AAG | ACT | CTG | TTT | GTA | GAA | TTC | ACG | GTT | CAC | CTT | TTC | AAC | ATC | 240 |
| Tyr 65 | Lys | Lys | Thr | Leu | Phe 70 | Val | Glu | Phe | Thr | Val 75 | His | Leu | Phe | Asn | Ile 80 | |
| GCT | AAG | CCA | AGG | CCA | CCC | TGG | ATG | GGT | CTG | CTA | GGT | CCT | ACC | ATC | CAG | 288 |
| Ala | Lys | Pro | Arg | Pro 85 | Pro | Trp | Met | Gly | Leu 90 | Leu | Gly | Pro | Thr | Ile 95 | Gln | |
| GCT | GAG | GTT | TAT | GAT | ACA | GTG | GTC | ATT | ACA | CTT | AAG | AAC | ATG | GCT | TCC | 336 |
| Ala | Glu | Val | Tyr 100 | Asp | Thr | Val | Val | Ile 105 | Thr | Leu | Lys | Asn | Met 110 | Ala | Ser | |
| CAT | CCT | GTC | AGT | CTT | CAT | GCT | GTT | GGT | GTA | TCC | TAC | TGG | AAA | GCT | TCT | 384 |
| His | Pro | Val 115 | Ser | Leu | His | Ala | Val 120 | Gly | Val | Ser | Tyr | Trp 125 | Lys | Ala | Ser | |
| GAG | GGA | GCT | GAA | TAT | GAT | GAT | CAG | ACC | AGT | CAA | AGG | GAG | AAA | GAA | GAT | 432 |
| Glu | Gly 130 | Ala | Glu | Tyr | Asp | Asp 135 | Gln | Thr | Ser | Gln | Arg 140 | Glu | Lys | Glu | Asp | |
| GAT | AAA | GTC | TTC | CCT | GGT | GGA | AGC | CAT | ACA | TAT | GTC | TGG | CAG | GTC | CTG | 480 |
| Asp 145 | Lys | Val | Phe | Pro | Gly 150 | Gly | Ser | His | Thr | Tyr 155 | Val | Trp | Gln | Val | Leu 160 | |
| AAA | GAG | AAT | GGT | CCA | ATG | GCC | TCT | GAC | CCA | CTG | TGC | CTT | ACC | TAC | TCA | 528 |
| Lys | Glu | Asn | Gly | Pro 165 | Met | Ala | Ser | Asp | Pro 170 | Leu | Cys | Leu | Thr | Tyr 175 | Ser | |
| TAT | CTT | TCT | CAT | GTG | GAC | CTG | GTA | AAA | GAC | TTG | AAT | TCA | GGC | CTC | ATT | 576 |
| Tyr | Leu | Ser | His 180 | Val | Asp | Leu | Val | Lys 185 | Asp | Leu | Asn | Ser | Gly 190 | Leu | Ile | |
| GGA | GCC | CTA | CTA | GTA | TGT | AGA | GAA | GGG | AGT | CTG | GCC | AAG | GAA | AAG | ACA | 624 |
| Gly | Ala | Leu 195 | Leu | Val | Cys | Arg | Glu 200 | Gly | Ser | Leu | Ala | Lys 205 | Glu | Lys | Thr | |
| CAG | ACC | TTG | CAC | AAA | TTT | ATA | CTA | CTT | TTT | GCT | GTA | TTT | GAT | GAA | GGG | 672 |
| Gln | Thr | Leu 210 | His | Lys | Phe | Ile | Leu 215 | Leu | Phe | Ala | Val | Phe 220 | Asp | Glu | Gly | |
| AAA | AGT | TGG | CAC | TCA | GAA | ACA | AAG | AAC | TCC | TTG | ATG | CAG | GAT | AGG | GAT | 720 |
| Lys 225 | Ser | Trp | His | Ser | Glu 230 | Thr | Lys | Asn | Ser | Leu 235 | Met | Gln | Asp | Arg | Asp 240 | |
| GCT | GCA | TCT | GCT | CGG | GCC | TGG | CCT | AAA | ATG | CAC | ACA | GTC | AAT | GGT | TAT | 768 |
| Ala | Ala | Ser | Ala | Arg 245 | Ala | Trp | Pro | Lys | Met 250 | His | Thr | Val | Asn | Gly 255 | Tyr | |
| GTA | AAC | AGG | TCT | CTG | CCA | GGT | CTG | ATT | GGA | TGC | CAC | AGG | AAA | TCA | GTC | 816 |
| Val | Asn | Arg | Ser 260 | Leu | Pro | Gly | Leu | Ile 265 | Gly | Cys | His | Arg | Lys 270 | Ser | Val | |
| TAT | TGG | CAT | GTG | ATT | GGA | ATG | GGC | ACC | ACT | CCT | GAA | GTG | CAC | TCA | ATA | 864 |
| Tyr | Trp | His 275 | Val | Ile | Gly | Met | Gly 280 | Thr | Thr | Pro | Glu | Val 285 | His | Ser | Ile | |
| TTC | CTC | GAA | GGT | CAC | ACA | TTT | CTT | GTG | AGG | AAC | CAT | CGC | CAG | GCG | TCC | 912 |
| Phe | Leu | Glu 290 | Gly | His | Thr | Phe | Leu 295 | Val | Arg | Asn | His | Arg 300 | Gln | Ala | Ser | |
| TTG | GAA | ATC | TCG | CCA | ATA | ACT | TTC | CTT | ACT | GCT | CAA | ACA | CTC | TTG | ATG | 960 |
| Leu 305 | Glu | Ile | Ser | Pro | Ile 310 | Thr | Phe | Leu | Thr | Ala 315 | Gln | Thr | Leu | Leu | Met 320 | |
| GAC | CTT | GGA | CAG | TTT | CTA | CTG | TTT | TGT | CAT | ATC | TCT | TCC | CAC | CAA | CAT | 1008 |
| Asp | Leu | Gly | Gln | Phe 325 | Leu | Leu | Phe | Cys | His 330 | Ile | Ser | Ser | His | Gln 335 | His | |
| GAT | GGC | ATG | GAA | GCT | TAT | GTC | AAA | GTA | GAC | AGC | TGT | CCA | GAG | GAA | CCC | 1056 |
| Asp | Gly | Met | Glu 340 | Ala | Tyr | Val | Lys | Val 345 | Asp | Ser | Cys | Pro | Glu 350 | Glu | Pro | |

| | | | | | | | | | | | | | | | | |
|---|---|---|---|---|---|---|---|---|---|---|---|---|---|---|---|---|
| CAA | CTA | CGA | ATG | AAA | AAT | AAT | GAA | GAA | GCG | GAA | GAC | TAT | GAT | GAT | GAT | 1104 |
| Gln | Leu | Arg | Met | Lys | Asn | Asn | Glu | Glu | Ala | Glu | Asp | Tyr | Asp | Asp | Asp | |
| | | 355 | | | | 360 | | | | | 365 | | | | | |
| CTT | ACT | GAT | TCT | GAA | ATG | GAT | GTG | GTC | AGG | TTT | GAT | GAT | GAC | AAC | TCT | 1152 |
| Leu | Thr | Asp | Ser | Glu | Met | Asp | Val | Val | Arg | Phe | Asp | Asp | Asp | Asn | Ser | |
| | 370 | | | | | 375 | | | | | | 380 | | | | |
| CCT | TCC | TTT | ATC | CAA | ATT | CGC | TCA | GTT | GCC | AAG | AAG | CAT | CCT | AAA | ACT | 1200 |
| Pro | Ser | Phe | Ile | Gln | Ile | Arg | Ser | Val | Ala | Lys | Lys | His | Pro | Lys | Thr | |
| 385 | | | | | 390 | | | | | 395 | | | | | 400 | |
| TGG | GTA | CAT | TAC | ATT | GCT | GCT | GAA | GAG | GAG | GAC | TGG | GAC | TAT | GCT | CCC | 1248 |
| Trp | Val | His | Tyr | Ile | Ala | Ala | Glu | Glu | Glu | Asp | Trp | Asp | Tyr | Ala | Pro | |
| | | | | 405 | | | | | 410 | | | | | 415 | | |
| TTA | GTC | CTC | GCC | CCC | GAT | GAC | AGA | AGT | TAT | AAA | AGT | CAA | TAT | TTG | AAC | 1296 |
| Leu | Val | Leu | Ala | Pro | Asp | Asp | Arg | Ser | Tyr | Lys | Ser | Gln | Tyr | Leu | Asn | |
| | | | 420 | | | | | 425 | | | | | 430 | | | |
| AAT | GGC | CCT | CAG | CGG | ATT | GGT | AGG | AAG | TAC | AAA | AAA | GTC | CGA | TTT | ATG | 1344 |
| Asn | Gly | Pro | Gln | Arg | Ile | Gly | Arg | Lys | Tyr | Lys | Lys | Val | Arg | Phe | Met | |
| | | 435 | | | | | 440 | | | | | 445 | | | | |
| GCA | TAC | ACA | GAT | GAA | ACC | TTT | AAG | ACT | CGT | GAA | GCT | ATT | CAG | CAT | GAA | 1392 |
| Ala | Tyr | Thr | Asp | Glu | Thr | Phe | Lys | Thr | Arg | Glu | Ala | Ile | Gln | His | Glu | |
| | 450 | | | | | 455 | | | | | 460 | | | | | |
| TCA | GGA | ATC | TTG | GGA | CCT | TTA | CTT | TAT | GGG | GAA | GTT | GGA | GAC | ACA | CTG | 1440 |
| Ser | Gly | Ile | Leu | Gly | Pro | Leu | Leu | Tyr | Gly | Glu | Val | Gly | Asp | Thr | Leu | |
| 465 | | | | | 470 | | | | | 475 | | | | | 480 | |
| TTG | ATT | ATA | TTT | AAG | AAT | CAA | GCA | AGC | AGA | CCA | TAT | AAC | ATC | TAC | CCT | 1488 |
| Leu | Ile | Ile | Phe | Lys | Asn | Gln | Ala | Ser | Arg | Pro | Tyr | Asn | Ile | Tyr | Pro | |
| | | | | 485 | | | | | 490 | | | | | 495 | | |
| CAC | GGA | ATC | ACT | GAT | GTC | CGT | CCT | TTG | TAT | TCA | AGG | AGA | TTA | CCA | AAA | 1536 |
| His | Gly | Ile | Thr | Asp | Val | Arg | Pro | Leu | Tyr | Ser | Arg | Arg | Leu | Pro | Lys | |
| | | | 500 | | | | | 505 | | | | | 510 | | | |
| GGT | GTA | AAA | CAT | TTG | AAG | GAT | TTT | CCA | ATT | CTG | CCA | GGA | GAA | ATA | TTC | 1584 |
| Gly | Val | Lys | His | Leu | Lys | Asp | Phe | Pro | Ile | Leu | Pro | Gly | Glu | Ile | Phe | |
| | | 515 | | | | | 520 | | | | | 525 | | | | |
| AAA | TAT | AAA | TGG | ACA | GTG | ACT | GTA | GAA | GAT | GGG | CCA | ACT | AAA | TCA | GAT | 1632 |
| Lys | Tyr | Lys | Trp | Thr | Val | Thr | Val | Glu | Asp | Gly | Pro | Thr | Lys | Ser | Asp | |
| | 530 | | | | | 535 | | | | | 540 | | | | | |
| CCT | CGG | TGC | CTG | ACC | CGC | TAT | TAC | TCT | AGT | TTC | GTT | AAT | ATG | GAG | AGA | 1680 |
| Pro | Arg | Cys | Leu | Thr | Arg | Tyr | Tyr | Ser | Ser | Phe | Val | Asn | Met | Glu | Arg | |
| 545 | | | | | 550 | | | | | 555 | | | | | 560 | |
| GAT | CTA | GCT | TCA | GGA | CTC | ATT | GGC | CCT | CTC | CTC | ATC | TGC | TAC | AAA | GAA | 1728 |
| Asp | Leu | Ala | Ser | Gly | Leu | Ile | Gly | Pro | Leu | Leu | Ile | Cys | Tyr | Lys | Glu | |
| | | | | 565 | | | | | 570 | | | | | 575 | | |
| TCT | GTA | GAT | CAA | AGA | GGA | AAC | CAG | ATA | ATG | TCA | GAC | AAG | AGG | AAT | GTC | 1776 |
| Ser | Val | Asp | Gln | Arg | Gly | Asn | Gln | Ile | Met | Ser | Asp | Lys | Arg | Asn | Val | |
| | | | 580 | | | | | 585 | | | | | 590 | | | |
| ATC | CTG | TTT | TCT | GTA | TTT | GAT | GAG | AAC | CGA | AGC | TGG | TAC | CTC | ACA | GAG | 1824 |
| Ile | Leu | Phe | Ser | Val | Phe | Asp | Glu | Asn | Arg | Ser | Trp | Tyr | Leu | Thr | Glu | |
| | | 595 | | | | | 600 | | | | | 605 | | | | |
| AAT | ATA | CAA | CGC | TTT | CTC | CCC | AAT | CCA | GCT | GGA | GTG | CAG | CTT | GAG | GAT | 1872 |
| Asn | Ile | Gln | Arg | Phe | Leu | Pro | Asn | Pro | Ala | Gly | Val | Gln | Leu | Glu | Asp | |
| | 610 | | | | | 615 | | | | | 620 | | | | | |
| CCA | GAG | TTC | CAA | GCC | TCC | AAC | ATC | ATG | CAC | AGC | ATC | AAT | GGC | TAT | GTT | 1920 |
| Pro | Glu | Phe | Gln | Ala | Ser | Asn | Ile | Met | His | Ser | Ile | Asn | Gly | Tyr | Val | |
| 625 | | | | | 630 | | | | | 635 | | | | | 640 | |
| TTT | GAT | AGT | TTG | CAG | TTG | TCA | GTT | TGT | TTG | CAT | GAG | GTG | GCA | TAC | TGG | 1968 |
| Phe | Asp | Ser | Leu | Gln | Leu | Ser | Val | Cys | Leu | His | Glu | Val | Ala | Tyr | Trp | |
| | | | | 645 | | | | | 650 | | | | | 655 | | |
| TAC | ATT | CTA | AGC | ATT | GGA | GCA | CAG | ACT | GAC | TTC | CTT | TCT | GTC | TTC | TTC | 2016 |
| Tyr | Ile | Leu | Ser | Ile | Gly | Ala | Gln | Thr | Asp | Phe | Leu | Ser | Val | Phe | Phe | |
| | | | | 660 | | | | | 665 | | | | | 670 | | |

```
TCT GGA TAT ACC TTC AAA CAC AAA ATG GTC TAT GAA GAC ACA CTC ACC    2064
Ser Gly Tyr Thr Phe Lys His Lys Met Val Tyr Glu Asp Thr Leu Thr
        675             680                 685

CTA TTC CCA TTC TCA GGA GAA ACT GTC TTC ATG TCG ATG GAA AAC CCA    2112
Leu Phe Pro Phe Ser Gly Glu Thr Val Phe Met Ser Met Glu Asn Pro
    690             695                 700

GGT CTA TGG ATT CTG GGG TGC CAC AAC TCA GAC TTT CGG AAC AGA GGC    2160
Gly Leu Trp Ile Leu Gly Cys His Asn Ser Asp Phe Arg Asn Arg Gly
705             710                 715                 720

ATG ACC GCC TTA CTG AAG GTT TCT AGT TGT GAC AAG AAC ACT GGT GAT    2208
Met Thr Ala Leu Leu Lys Val Ser Ser Cys Asp Lys Asn Thr Gly Asp
                725                 730                 735

TAT TAC GAG GAC AGT TAT GAA GAT ATT TCA GCA TAC TTG CTG AGT AAA    2256
Tyr Tyr Glu Asp Ser Tyr Glu Asp Ile Ser Ala Tyr Leu Leu Ser Lys
            740                 745                 750

AAC AAT GCC ATT GAA CCA AGA AGC TTC TCC CAG AAT TCA AGA CAC CCT    2304
Asn Asn Ala Ile Glu Pro Arg Ser Phe Ser Gln Asn Ser Arg His Pro
        755                 760                 765

AGC ACT AGG CAA AAG CAA TTT AAT GCC ACC ACA ATT CCA GAA AAT GAC    2352
Ser Thr Arg Gln Lys Gln Phe Asn Ala Thr Thr Ile Pro Glu Asn Asp
770             775                 780

ATA GAG AAG ACT GAC CCT TGG TTT GCA CAC AGA ACA CCT ATG CCT AAA    2400
Ile Glu Lys Thr Asp Pro Trp Phe Ala His Arg Thr Pro Met Pro Lys
785             790                 795                 800

ATA CAA AAT GTC TCC TCT AGT GAT TTG TTG ATG CTC TTG CGA CAG AGT    2448
Ile Gln Asn Val Ser Ser Ser Asp Leu Leu Met Leu Leu Arg Gln Ser
                805                 810                 815

CCT ACT CCA CAT GGG CTA TCC TTA TCT GAT CTC CAA GAA GCC AAA TAT    2496
Pro Thr Pro His Gly Leu Ser Leu Ser Asp Leu Gln Glu Ala Lys Tyr
            820                 825                 830

GAG ACT TTT TCT GAT GAT CCA TCA CCT GGA GCA ATA GAC AGT AAT AAC    2544
Glu Thr Phe Ser Asp Asp Pro Ser Pro Gly Ala Ile Asp Ser Asn Asn
        835                 840                 845

AGC CTG TCT GAA ATG ACA CAC TTC AGG CCA CAG CTC CAT CAC AGT GGG    2592
Ser Leu Ser Glu Met Thr His Phe Arg Pro Gln Leu His His Ser Gly
850                 855                 860

GAC ATG GTA TTT ACC CCT GAG TCA GGC CTC CAA TTA AGA TTA AAT GAG    2640
Asp Met Val Phe Thr Pro Glu Ser Gly Leu Gln Leu Arg Leu Asn Glu
865             870                 875                 880

AAA CTG GGG ACA ACT GCA GCA ACA GAG TTG AAG AAA CTT GAT TTC AAA    2688
Lys Leu Gly Thr Thr Ala Ala Thr Glu Leu Lys Lys Leu Asp Phe Lys
                885                 890                 895

GTT TCT AGT ACA TCA AAT AAT CTG ATT TCA ACA ATT CCA TCA GAC AAT    2736
Val Ser Ser Thr Ser Asn Asn Leu Ile Ser Thr Ile Pro Ser Asp Asn
            900                 905                 910

TTG GCA GCA GGT ACT GAT AAT ACA AGT CCT TTA GGA CCC CCA AGT ATG    2784
Leu Ala Ala Gly Thr Asp Asn Thr Ser Ser Leu Gly Pro Pro Ser Met
        915                 920                 925

CCA GTT CAT TAT GAT AGT CAA TTA GAT ACC ACT CTA TTT GGC AAA AAG    2832
Pro Val His Tyr Asp Ser Gln Leu Asp Thr Thr Leu Phe Gly Lys Lys
    930                 935                 940

TCA TCT CCC CTT ACT GAG TCT GGT GGA CCT CTG AGC TTG AGT GAA GAA    2880
Ser Ser Pro Leu Thr Glu Ser Gly Gly Pro Leu Ser Leu Ser Glu Glu
945                 950                 955                 960

AAT AAT GAT TCA AAG TTG TTA GAA TCA GGT TTA ATG AAT AGC CAA GAA    2928
Asn Asn Asp Ser Lys Leu Leu Glu Ser Gly Leu Met Asn Ser Gln Glu
                965                 970                 975

AGT TCA TGG GGA AAA AAT GTA TCG TCA ACA GAG AGT GGT AGG TTA TTT    2976
Ser Ser Trp Gly Lys Asn Val Ser Ser Thr Glu Ser Gly Arg Leu Phe
            980                 985                 990
```

| | | | | | | | | | | | | | | | | |
|---|---|---|---|---|---|---|---|---|---|---|---|---|---|---|---|---|
| AAA | GGG | AAA | AGA | GCT | CAT | GGA | CCT | GCT | TTG | TTG | ACT | AAA | GAT | AAT | GCC | 3024 |
| Lys | Gly | Lys | Arg | Ala | His | Gly | Pro | Ala | Leu | Leu | Thr | Lys | Asp | Asn | Ala | |
| | | 995 | | | | 1000 | | | | | 1005 | | | | | |
| TTA | TTC | AAA | GTT | AGC | ATC | TCT | TTG | TTA | AAG | ACA | AAC | AAA | ACT | TCC | AAT | 3072 |
| Leu | Phe | Lys | Val | Ser | Ile | Ser | Leu | Leu | Lys | Thr | Asn | Lys | Thr | Ser | Asn | |
| 1010 | | | | | 1015 | | | | | 1020 | | | | | | |
| AAT | TCA | GCA | ACT | AAT | AGA | AAG | ACT | CAC | ATT | GAT | GGC | CCA | TCA | TTA | TTA | 3120 |
| Asn | Ser | Ala | Thr | Asn | Arg | Lys | Thr | His | Ile | Asp | Gly | Pro | Ser | Leu | Leu | |
| 1025 | | | | | 1030 | | | | | 1035 | | | | | 1040 | |
| ATT | GAG | AAT | AGT | CCA | TCA | GTC | TGG | CAA | AAT | ATA | TTA | GAA | AGT | GAC | ACT | 3168 |
| Ile | Glu | Asn | Ser | Pro | Ser | Val | Trp | Gln | Asn | Ile | Leu | Glu | Ser | Asp | Thr | |
| | | | | 1045 | | | | | 1050 | | | | | 1055 | | |
| GAG | TTT | AAA | AAA | GTG | ACA | CCT | TTG | ATT | CAT | GAC | AGA | ATG | CTT | ATG | GAC | 3216 |
| Glu | Phe | Lys | Lys | Val | Thr | Pro | Leu | Ile | His | Asp | Arg | Met | Leu | Met | Asp | |
| | | | | 1060 | | | | | 1065 | | | | | 1070 | | |
| AAA | AAT | GCT | ACA | GCT | TTG | AGG | CTA | AAT | CAT | ATG | TCA | AAT | AAA | ACT | ACT | 3264 |
| Lys | Asn | Ala | Thr | Ala | Leu | Arg | Leu | Asn | His | Met | Ser | Asn | Lys | Thr | Thr | |
| | | | 1075 | | | | | 1080 | | | | | 1085 | | | |
| TCA | TCA | AAA | AAC | ATG | GAA | ATG | GTC | CAA | CAG | AAA | AAA | GAG | GGC | CCC | ATT | 3312 |
| Ser | Ser | Lys | Asn | Met | Glu | Met | Val | Gln | Gln | Lys | Lys | Glu | Gly | Pro | Ile | |
| | | 1090 | | | | | 1095 | | | | | 1100 | | | | |
| CCA | CCA | GAT | GCA | CAA | AAT | CCA | GAT | ATG | TCG | TTC | TTT | AAG | ATG | CTA | TTC | 3360 |
| Pro | Pro | Asp | Ala | Gln | Asn | Pro | Asp | Met | Ser | Phe | Phe | Lys | Met | Leu | Phe | |
| 1105 | | | | | 1110 | | | | | 1115 | | | | | 1120 | |
| TTG | CCA | GAA | TCA | GCA | AGG | TGG | ATA | CAA | AGG | ACT | CAT | GGA | AAG | AAC | TCT | 3408 |
| Leu | Pro | Glu | Ser | Ala | Arg | Trp | Ile | Gln | Arg | Thr | His | Gly | Lys | Asn | Ser | |
| | | | | 1125 | | | | | 1130 | | | | | 1135 | | |
| CTG | AAC | TCT | GGG | CAA | GGC | CCC | AGT | CCA | AAG | CAA | TTA | GTA | TCC | TTA | GGA | 3456 |
| Leu | Asn | Ser | Gly | Gln | Gly | Pro | Ser | Pro | Lys | Gln | Leu | Val | Ser | Leu | Gly | |
| | | | 1140 | | | | | 1145 | | | | | 1150 | | | |
| CCA | GAA | AAA | TCT | GTG | GAA | GGT | CAG | AAT | TTC | TTG | TCT | GAG | AAA | AAC | AAA | 3504 |
| Pro | Glu | Lys | Ser | Val | Glu | Gly | Gln | Asn | Phe | Leu | Ser | Glu | Lys | Asn | Lys | |
| | | 1155 | | | | | 1160 | | | | | 1165 | | | | |
| GTG | GTA | GTA | GGA | AAG | GGT | GAA | TTT | ACA | AAG | GAC | GTA | GGA | CTC | AAA | GAG | 3552 |
| Val | Val | Val | Gly | Lys | Gly | Glu | Phe | Thr | Lys | Asp | Val | Gly | Leu | Lys | Glu | |
| | | 1170 | | | | | 1175 | | | | | 1180 | | | | |
| ATG | GTT | TTT | CCA | AGC | AGC | AGA | AAC | CTA | TTT | CTT | ACT | AAC | TTG | GAT | AAT | 3600 |
| Met | Val | Phe | Pro | Ser | Ser | Arg | Asn | Leu | Phe | Leu | Thr | Asn | Leu | Asp | Asn | |
| 1185 | | | | | 1190 | | | | | 1195 | | | | | 1200 | |
| TTA | CAT | GAA | AAT | AAT | ACA | CAC | AAT | CAA | GAA | AAA | AAA | ATT | CAG | GAA | GAA | 3648 |
| Leu | His | Glu | Asn | Asn | Thr | His | Asn | Gln | Glu | Lys | Lys | Ile | Gln | Glu | Glu | |
| | | | | 1205 | | | | | 1210 | | | | | 1215 | | |
| ATA | GAA | AAG | AAG | GAA | ACA | TTA | ATC | CAA | GAG | AAT | GTA | GTT | TTG | CCT | CAG | 3696 |
| Ile | Glu | Lys | Lys | Glu | Thr | Leu | Ile | Gln | Glu | Asn | Val | Val | Leu | Pro | Gln | |
| | | | 1220 | | | | | 1225 | | | | | 1230 | | | |
| ATA | CAT | ACA | GTG | ACT | GGC | ACT | AAG | AAT | TTC | ATG | AAG | AAC | CTT | TTC | TTA | 3744 |
| Ile | His | Thr | Val | Thr | Gly | Thr | Lys | Asn | Phe | Met | Lys | Asn | Leu | Phe | Leu | |
| | | 1235 | | | | | 1240 | | | | | 1245 | | | | |
| CTG | AGC | ACT | AGG | CAA | AAT | GTA | GAA | GGT | TCA | TAT | GAG | GGG | GCA | TAT | GCT | 3792 |
| Leu | Ser | Thr | Arg | Gln | Asn | Val | Glu | Gly | Ser | Tyr | Glu | Gly | Ala | Tyr | Ala | |
| | | | 1250 | | | | | 1255 | | | | | 1260 | | | |
| CCA | GTA | CTT | CAA | GAT | TTT | AGG | TCA | TTA | AAT | GAT | TCA | ACA | AAT | AGA | ACA | 3840 |
| Pro | Val | Leu | Gln | Asp | Phe | Arg | Ser | Leu | Asn | Asp | Ser | Thr | Asn | Arg | Thr | |
| 1265 | | | | | 1270 | | | | | 1275 | | | | | 1280 | |
| AAG | AAA | CAC | ACA | GCT | CAT | TTC | TCA | AAA | AAA | GGG | GAG | GAA | GAA | AAC | TTG | 3888 |
| Lys | Lys | His | Thr | Ala | His | Phe | Ser | Lys | Lys | Gly | Glu | Glu | Glu | Asn | Leu | |
| | | | | 1285 | | | | | 1290 | | | | | 1295 | | |
| GAA | GGC | TTG | GGA | AAT | CAA | ACC | AAG | CAA | ATT | GTA | GAG | AAA | TAT | GCA | TGC | 3936 |
| Glu | Gly | Leu | Gly | Asn | Gln | Thr | Lys | Gln | Ile | Val | Glu | Lys | Tyr | Ala | Cys | |
| | | | 1300 | | | | | 1305 | | | | | 1310 | | | |

| | | | | | | | | | | | | | | | | |
|---|---|---|---|---|---|---|---|---|---|---|---|---|---|---|---|---|
| ACC | ACA | AGG | ATA | TCT | CCT | AAT | ACA | AGC | CAG | CAG | AAT | TTT | GTC | ACG | CAA | 3984 |
| Thr | Thr | Arg | Ile | Ser | Pro | Asn | Thr | Ser | Gln | Gln | Asn | Phe | Val | Thr | Gln | |
| | | 1315 | | | | 1320 | | | | | | 1325 | | | | |
| CGT | AGT | AAG | AGA | GCT | TTG | AAA | CAA | TTC | AGA | CTC | CCA | CTA | GAA | GAA | ACA | 4032 |
| Arg | Ser | Lys | Arg | Ala | Leu | Lys | Gln | Phe | Arg | Leu | Pro | Leu | Glu | Glu | Thr | |
| | | 1330 | | | | 1335 | | | | | | 1340 | | | | |
| GAA | CTT | GAA | AAA | AGG | ATA | ATT | GTG | GAT | GAC | ACC | TCA | ACC | CAG | TGG | TCC | 4080 |
| Glu | Leu | Glu | Lys | Arg | Ile | Ile | Val | Asp | Asp | Thr | Ser | Thr | Gln | Trp | Ser | |
| 1345 | | | | | 1350 | | | | | 1355 | | | | | 1360 | |
| AAA | AAC | ATG | AAA | CAT | TTG | ACC | CCG | AGC | ACC | CTC | ACA | CAG | ATA | GAC | TAC | 4128 |
| Lys | Asn | Met | Lys | His | Leu | Thr | Pro | Ser | Thr | Leu | Thr | Gln | Ile | Asp | Tyr | |
| | | | | 1365 | | | | | 1370 | | | | | 1375 | | |
| AAT | GAG | AAG | GAG | AAA | GGG | GCC | ATT | ACT | CAG | TCT | CCC | TTA | TCA | GAT | TGC | 4176 |
| Asn | Glu | Lys | Glu | Lys | Gly | Ala | Ile | Thr | Gln | Ser | Pro | Leu | Ser | Asp | Cys | |
| | | | 1380 | | | | | 1385 | | | | | 1390 | | | |
| CTT | ACG | AGG | AGT | CAT | AGC | ATC | CCT | CAA | GCA | AAT | AGA | TCT | CCA | TTA | CCC | 4224 |
| Leu | Thr | Arg | Ser | His | Ser | Ile | Pro | Gln | Ala | Asn | Arg | Ser | Pro | Leu | Pro | |
| | | 1395 | | | | 1400 | | | | | | 1405 | | | | |
| ATT | GCA | AAG | GTA | TCA | TCA | TTT | CCA | TCT | ATT | AGA | CCT | ATA | TAT | CTG | ACC | 4272 |
| Ile | Ala | Lys | Val | Ser | Ser | Phe | Pro | Ser | Ile | Arg | Pro | Ile | Tyr | Leu | Thr | |
| | | 1410 | | | | 1415 | | | | | | 1420 | | | | |
| AGG | GTC | CTA | TTC | CAA | GAC | AAC | TCT | TCT | CAT | CTT | CCA | GCA | GCA | TCT | TAT | 4320 |
| Arg | Val | Leu | Phe | Gln | Asp | Asn | Ser | Ser | His | Leu | Pro | Ala | Ala | Ser | Tyr | |
| 1425 | | | | | 1430 | | | | | 1435 | | | | | 1440 | |
| AGA | AAG | AAA | GAT | TCT | GGG | GTC | CAA | GAA | AGC | AGT | CAT | TTC | TTA | CAA | GGA | 4368 |
| Arg | Lys | Lys | Asp | Ser | Gly | Val | Gln | Glu | Ser | Ser | His | Phe | Leu | Gln | Gly | |
| | | | | 1445 | | | | | 1450 | | | | | 1455 | | |
| GCC | AAA | AAA | AAT | AAC | CTT | TCT | TTA | GCC | ATT | CTA | ACC | TTG | GAG | ATG | ACT | 4416 |
| Ala | Lys | Lys | Asn | Asn | Leu | Ser | Leu | Ala | Ile | Leu | Thr | Leu | Glu | Met | Thr | |
| | | | 1460 | | | | | 1465 | | | | | 1470 | | | |
| GGT | GAT | CAA | AGA | GAG | GTT | GGC | TCC | CTG | GGG | ACA | AGT | GCC | ACA | AAT | TCA | 4464 |
| Gly | Asp | Gln | Arg | Glu | Val | Gly | Ser | Leu | Gly | Thr | Ser | Ala | Thr | Asn | Ser | |
| | | 1475 | | | | 1480 | | | | | | 1485 | | | | |
| GTC | ACA | TAC | AAG | AAA | GTT | GAG | AAC | ACT | GTT | CTC | CCG | AAA | CCA | GAC | TTG | 4512 |
| Val | Thr | Tyr | Lys | Lys | Val | Glu | Asn | Thr | Val | Leu | Pro | Lys | Pro | Asp | Leu | |
| | | 1490 | | | | 1495 | | | | | | 1500 | | | | |
| CCC | AAA | ACA | TCT | GGC | AAA | GTT | GAA | TTG | CTT | CCA | AAA | GTT | CAC | ATT | TAT | 4560 |
| Pro | Lys | Thr | Ser | Gly | Lys | Val | Glu | Leu | Leu | Pro | Lys | Val | His | Ile | Tyr | |
| 1505 | | | | | 1510 | | | | | 1515 | | | | | 1520 | |
| CAG | AAG | GAC | CTA | TTC | CCT | ACG | GAA | ACT | AGC | AAT | GGG | TCT | CCT | GGC | CAT | 4608 |
| Gln | Lys | Asp | Leu | Phe | Pro | Thr | Glu | Thr | Ser | Asn | Gly | Ser | Pro | Gly | His | |
| | | | | 1525 | | | | | 1530 | | | | | 1535 | | |
| CTG | GAT | CTC | GTG | GAA | GGG | AGC | CTT | CTT | CAG | GGA | ACA | GAG | GGA | GCG | ATT | 4656 |
| Leu | Asp | Leu | Val | Glu | Gly | Ser | Leu | Leu | Gln | Gly | Thr | Glu | Gly | Ala | Ile | |
| | | | 1540 | | | | | 1545 | | | | | 1550 | | | |
| AAG | TGG | AAT | GAA | GCA | AAC | AGA | CCT | GGA | AAA | GTT | CCC | TTT | CTG | AGA | GTA | 4704 |
| Lys | Trp | Asn | Glu | Ala | Asn | Arg | Pro | Gly | Lys | Val | Pro | Phe | Leu | Arg | Val | |
| | | 1555 | | | | 1560 | | | | | | 1565 | | | | |
| GCA | ACA | GAA | AGC | TCT | GCA | AAG | ACT | CCC | TCC | AAG | CTA | TTG | GAT | CCT | CTT | 4752 |
| Ala | Thr | Glu | Ser | Ser | Ala | Lys | Thr | Pro | Ser | Lys | Leu | Leu | Asp | Pro | Leu | |
| | | 1570 | | | | 1575 | | | | | | 1580 | | | | |
| GCT | TGG | GAT | AAC | CAC | TAT | GGT | ACT | CAG | ATA | CCA | AAA | GAA | GAG | TGG | AAA | 4800 |
| Ala | Trp | Asp | Asn | His | Tyr | Gly | Thr | Gln | Ile | Pro | Lys | Glu | Glu | Trp | Lys | |
| 1585 | | | | | 1590 | | | | | 1595 | | | | | 1600 | |
| TCC | CAA | GAG | AAG | TCA | CCA | GAA | AAA | ACA | GCT | TTT | AAG | AAA | AAG | GAT | ACC | 4848 |
| Ser | Gln | Glu | Lys | Ser | Pro | Glu | Lys | Thr | Ala | Phe | Lys | Lys | Lys | Asp | Thr | |
| | | | | 1605 | | | | | 1610 | | | | | 1615 | | |
| ATT | TTG | TCC | CTG | AAC | GCT | TGT | GAA | AGC | AAT | CAT | GCA | ATA | GCA | GCA | ATA | 4896 |
| Ile | Leu | Ser | Leu | Asn | Ala | Cys | Glu | Ser | Asn | His | Ala | Ile | Ala | Ala | Ile | |
| | | | 1620 | | | | | 1625 | | | | | 1630 | | | |

| | | | | | | | | | | | | | | | | |
|---|---|---|---|---|---|---|---|---|---|---|---|---|---|---|---|---|
| AAT | GAG | GGA | CAA | AAT | AAG | CCC | GAA | ATA | GAA | GTC | ACC | TGG | GCA | AAG | CAA | 4944 |
| Asn | Glu | Gly | Gln | Asn | Lys | Pro | Glu | Ile | Glu | Val | Thr | Trp | Ala | Lys | Gln | |
| | | | 1635 | | | | 1640 | | | | | 1645 | | | | |
| GGT | AGG | ACT | GAA | AGG | CTG | TGC | TCT | CAA | AAC | CCA | CCA | GTC | TTG | AAA | CGC | 4992 |
| Gly | Arg | Thr | Glu | Arg | Leu | Cys | Ser | Gln | Asn | Pro | Pro | Val | Leu | Lys | Arg | |
| | | 1650 | | | | | 1655 | | | | | 1660 | | | | |
| CAT | CAA | CGG | GAA | ATA | ACT | CGT | ACT | ACT | CTT | CAG | TCA | GAT | CAA | GAG | GAA | 5040 |
| His | Gln | Arg | Glu | Ile | Thr | Arg | Thr | Thr | Leu | Gln | Ser | Asp | Gln | Glu | Glu | |
| 1665 | | | | | 1670 | | | | | 1675 | | | | | 1680 | |
| ATT | GAC | TAT | GAT | GAT | ACC | ATA | TCA | GTT | GAA | ATG | AAG | AAG | GAA | GAT | TTT | 5088 |
| Ile | Asp | Tyr | Asp | Asp | Thr | Ile | Ser | Val | Glu | Met | Lys | Lys | Glu | Asp | Phe | |
| | | | | 1685 | | | | 1690 | | | | | 1695 | | | |
| GAC | ATT | TAT | GAT | GAG | GAT | GAA | AAT | CAG | AGC | CCC | CGC | AGC | TTT | CAA | AAG | 5136 |
| Asp | Ile | Tyr | Asp | Glu | Asp | Glu | Asn | Gln | Ser | Pro | Arg | Ser | Phe | Gln | Lys | |
| | | | 1700 | | | | | 1705 | | | | | 1710 | | | |
| AAA | ACA | CGA | CAC | TAT | TTT | ATT | GCT | GCA | GTG | GAG | AGG | CTC | TGG | GAT | TAT | 5184 |
| Lys | Thr | Arg | His | Tyr | Phe | Ile | Ala | Ala | Val | Glu | Arg | Leu | Trp | Asp | Tyr | |
| | | | 1715 | | | | | 1720 | | | | | 1725 | | | |
| GGG | ATG | AGT | AGC | TCC | CCA | CAT | GTT | CTA | AGA | AAC | AGG | GCT | CAG | AGT | GGC | 5232 |
| Gly | Met | Ser | Ser | Ser | Pro | His | Val | Leu | Arg | Asn | Arg | Ala | Gln | Ser | Gly | |
| | | 1730 | | | | | 1735 | | | | | 1740 | | | | |
| AGT | GTC | CCT | CAG | TTC | AAG | AAA | GTT | GTT | TTC | CAG | GAA | TTT | ACT | GAT | GGC | 5280 |
| Ser | Val | Pro | Gln | Phe | Lys | Lys | Val | Val | Phe | Gln | Glu | Phe | Thr | Asp | Gly | |
| 1745 | | | | | 1750 | | | | | 1755 | | | | | 1760 | |
| TCC | TTT | ACT | CAG | CCC | TTA | TAC | CGT | GGA | GAA | CTA | AAT | GAA | CAT | TTG | GGA | 5328 |
| Ser | Phe | Thr | Gln | Pro | Leu | Tyr | Arg | Gly | Glu | Leu | Asn | Glu | His | Leu | Gly | |
| | | | | 1765 | | | | | 1770 | | | | | 1775 | | |
| CTC | CTG | GGG | CCA | TAT | ATA | AGA | GCA | GAA | GTT | GAA | GAT | AAT | ATC | ATG | GTA | 5376 |
| Leu | Leu | Gly | Pro | Tyr | Ile | Arg | Ala | Glu | Val | Glu | Asp | Asn | Ile | Met | Val | |
| | | | 1780 | | | | | 1785 | | | | | 1790 | | | |
| ACT | TTC | AGA | AAT | CAG | GCC | TCT | CGT | CCC | TAT | TCC | TTC | TAT | TCT | AGC | CTT | 5424 |
| Thr | Phe | Arg | Asn | Gln | Ala | Ser | Arg | Pro | Tyr | Ser | Phe | Tyr | Ser | Ser | Leu | |
| | | | 1795 | | | | | 1800 | | | | | 1805 | | | |
| ATT | TCT | TAT | GAG | GAA | GAT | CAG | AGG | CAA | GGA | GCA | GAA | CCT | AGA | AAA | AAC | 5472 |
| Ile | Ser | Tyr | Glu | Glu | Asp | Gln | Arg | Gln | Gly | Ala | Glu | Pro | Arg | Lys | Asn | |
| | | | 1810 | | | | | 1815 | | | | | 1820 | | | |
| TTT | GTC | AAG | CCT | AAT | GAA | ACC | AAA | ACT | TAC | TTT | TGG | AAA | GTG | CAA | CAT | 5520 |
| Phe | Val | Lys | Pro | Asn | Glu | Thr | Lys | Thr | Tyr | Phe | Trp | Lys | Val | Gln | His | |
| 1825 | | | | | 1830 | | | | | 1835 | | | | | 1840 | |
| CAT | ATG | GCA | CCC | ACT | AAA | GAT | GAG | TTT | GAC | TGC | AAA | GCC | TGG | GCT | TAT | 5568 |
| His | Met | Ala | Pro | Thr | Lys | Asp | Glu | Phe | Asp | Cys | Lys | Ala | Trp | Ala | Tyr | |
| | | | | 1845 | | | | | 1850 | | | | | 1855 | | |
| TTC | TCT | GAT | GTT | GAC | CTG | GAA | AAA | GAT | GTG | CAC | TCA | GGC | CTG | ATT | GGA | 5616 |
| Phe | Ser | Asp | Val | Asp | Leu | Glu | Lys | Asp | Val | His | Ser | Gly | Leu | Ile | Gly | |
| | | | 1860 | | | | | 1865 | | | | | 1870 | | | |
| CCC | CTT | CTG | GTC | TGC | CAC | ACT | AAC | ACA | CTG | AAC | CCT | GCT | CAT | GGG | AGA | 5664 |
| Pro | Leu | Leu | Val | Cys | His | Thr | Asn | Thr | Leu | Asn | Pro | Ala | His | Gly | Arg | |
| | | | 1875 | | | | | 1880 | | | | | 1885 | | | |
| CAA | GTG | ACA | GTA | CAG | GAA | TTT | GCT | CTG | TTT | TTC | ACC | ATC | TTT | GAT | GAG | 5712 |
| Gln | Val | Thr | Val | Gln | Glu | Phe | Ala | Leu | Phe | Phe | Thr | Ile | Phe | Asp | Glu | |
| | | 1890 | | | | | 1895 | | | | | 1900 | | | | |
| ACC | AAA | AGC | TGG | TAC | TTC | ACT | GAA | AAT | ATG | GAA | AGA | AAC | TGC | AGG | GCT | 5760 |
| Thr | Lys | Ser | Trp | Tyr | Phe | Thr | Glu | Asn | Met | Glu | Arg | Asn | Cys | Arg | Ala | |
| 1905 | | | | | 1910 | | | | | 1915 | | | | | 1920 | |
| CCC | TGC | AAT | ATC | CAG | ATG | GAA | GAT | CCC | ACT | TTT | AAA | GAG | AAT | TAT | CGC | 5808 |
| Pro | Cys | Asn | Ile | Gln | Met | Glu | Asp | Pro | Thr | Phe | Lys | Glu | Asn | Tyr | Arg | |
| | | | | 1925 | | | | | 1930 | | | | | 1935 | | |
| TTC | CAT | GCA | ATC | AAT | GGC | TAC | ATA | ATG | GAT | ACA | CTA | CCT | GGC | TTA | GTA | 5856 |
| Phe | His | Ala | Ile | Asn | Gly | Tyr | Ile | Met | Asp | Thr | Leu | Pro | Gly | Leu | Val | |
| | | | | 1940 | | | | | 1945 | | | | | 1950 | | |

| | | | | | | | | | | | | | | | | |
|---|---|---|---|---|---|---|---|---|---|---|---|---|---|---|---|---|
| ATG | GCT | CAG | GAT | CAA | AGG | ATT | CGA | TGG | TAT | CTG | CTC | AGC | ATG | GGC | AGC | 5904 |
| Met | Ala | Gln | Asp | Gln | Arg | Ile | Arg | Trp | Tyr | Leu | Leu | Ser | Met | Gly | Ser | |
| | 1955 | | | | 1960 | | | | | 1965 | | | | | | |
| AAT | GAA | AAC | ATC | CAT | TCT | ATT | CAT | TTC | AGT | GGA | CAT | GTG | TTC | ACT | GTA | 5952 |
| Asn | Glu | Asn | Ile | His | Ser | Ile | His | Phe | Ser | Gly | His | Val | Phe | Thr | Val | |
| | 1970 | | | | 1975 | | | | | 1980 | | | | | | |
| CGA | AAA | AAA | GAG | GAG | TAT | AAA | ATG | GCA | CTG | TAC | AAT | CTC | TAT | CCA | GGT | 6000 |
| Arg | Lys | Lys | Glu | Glu | Tyr | Lys | Met | Ala | Leu | Tyr | Asn | Leu | Tyr | Pro | Gly | |
| 1985 | | | | | 1990 | | | | | 1995 | | | | | 2000 | |
| GTT | TTT | GAG | ACA | GTG | GAA | ATG | TTA | CCA | TCC | AAA | GCT | GGA | ATT | TGG | CGG | 6048 |
| Val | Phe | Glu | Thr | Val | Glu | Met | Leu | Pro | Ser | Lys | Ala | Gly | Ile | Trp | Arg | |
| | | | | 2005 | | | | | 2010 | | | | | 2015 | | |
| GTG | GAA | TGC | CTT | ATT | GGC | GAG | CAT | CTA | CAT | GCT | GGG | ATG | AGC | ACA | CTT | 6096 |
| Val | Glu | Cys | Leu | Ile | Gly | Glu | His | Leu | His | Ala | Gly | Met | Ser | Thr | Leu | |
| | | | 2020 | | | | | 2025 | | | | | 2030 | | | |
| TTT | CTG | GTG | TAC | AGC | AAT | AAG | TGT | CAG | ACT | CCC | CTG | GGA | ATG | GCT | TCT | 6144 |
| Phe | Leu | Val | Tyr | Ser | Asn | Lys | Cys | Gln | Thr | Pro | Leu | Gly | Met | Ala | Ser | |
| | | 2035 | | | | | 2040 | | | | | 2045 | | | | |
| GGA | CAC | ATT | AGA | GAT | TTT | CAG | ATT | ACA | GCT | TCA | GGA | CAA | TAT | GGA | CAG | 6192 |
| Gly | His | Ile | Arg | Asp | Phe | Gln | Ile | Thr | Ala | Ser | Gly | Gln | Tyr | Gly | Gln | |
| | 2050 | | | | | 2055 | | | | | 2060 | | | | | |
| TGG | GCC | CCA | AAG | CTG | GCC | AGA | CTT | CAT | TAT | TCC | GGA | TCA | ATC | AAT | GCC | 6240 |
| Trp | Ala | Pro | Lys | Leu | Ala | Arg | Leu | His | Tyr | Ser | Gly | Ser | Ile | Asn | Ala | |
| 2065 | | | | | 2070 | | | | | 2075 | | | | | 2080 | |
| TGG | AGC | ACC | AAG | GAG | CCC | TTT | TCT | TGG | ATC | AAG | GTG | GAT | CTG | TTG | GCA | 6288 |
| Trp | Ser | Thr | Lys | Glu | Pro | Phe | Ser | Trp | Ile | Lys | Val | Asp | Leu | Leu | Ala | |
| | | | | 2085 | | | | | 2090 | | | | | 2095 | | |
| CCA | ATG | ATT | ATT | CAC | GGC | ATC | AAG | ACC | CAG | GGT | GCC | CGT | CAG | AAG | TTC | 6336 |
| Pro | Met | Ile | Ile | His | Gly | Ile | Lys | Thr | Gln | Gly | Ala | Arg | Gln | Lys | Phe | |
| | | | 2100 | | | | | 2105 | | | | | 2110 | | | |
| TCC | AGC | CTC | TAC | ATC | TCT | CAG | TTT | ATC | ATC | ATG | TAT | AGT | CTT | GAT | GGG | 6384 |
| Ser | Ser | Leu | Tyr | Ile | Ser | Gln | Phe | Ile | Ile | Met | Tyr | Ser | Leu | Asp | Gly | |
| | | | 2115 | | | | | 2120 | | | | | 2125 | | | |
| AAG | AAG | TGG | CAG | ACT | TAT | CGA | GGA | AAT | TCC | ACT | GGA | ACC | TTA | ATG | GTC | 6432 |
| Lys | Lys | Trp | Gln | Thr | Tyr | Arg | Gly | Asn | Ser | Thr | Gly | Thr | Leu | Met | Val | |
| | | 2130 | | | | | 2135 | | | | | 2140 | | | | |
| TTC | TTT | GGC | AAT | GTG | GAT | TCA | TCT | GGG | ATA | AAA | CAC | AAT | ATT | TTT | AAC | 6480 |
| Phe | Phe | Gly | Asn | Val | Asp | Ser | Ser | Gly | Ile | Lys | His | Asn | Ile | Phe | Asn | |
| 2145 | | | | | 2150 | | | | | 2155 | | | | | 2160 | |
| CCT | CCA | ATT | ATT | GCT | CGA | TAC | ATC | CGT | TTG | CAC | CCA | ACT | CAT | TAT | AGC | 6528 |
| Pro | Pro | Ile | Ile | Ala | Arg | Tyr | Ile | Arg | Leu | His | Pro | Thr | His | Tyr | Ser | |
| | | | | 2165 | | | | | 2170 | | | | | 2175 | | |
| ATT | CGC | AGC | ACT | CTT | CGC | ATG | GAG | TTG | ATG | GGC | TGT | GAT | TTA | AAT | AGT | 6576 |
| Ile | Arg | Ser | Thr | Leu | Arg | Met | Glu | Leu | Met | Gly | Cys | Asp | Leu | Asn | Ser | |
| | | | | 2180 | | | | | 2185 | | | | | 2190 | | |
| TGC | AGC | ATG | CCA | TTG | GGA | ATG | GAG | AGT | AAA | GCA | ATA | TCA | GAT | GCA | CAG | 6624 |
| Cys | Ser | Met | Pro | Leu | Gly | Met | Glu | Ser | Lys | Ala | Ile | Ser | Asp | Ala | Gln | |
| | | | 2195 | | | | | 2200 | | | | | 2205 | | | |
| ATT | ACT | GCT | TCA | TCC | TAC | TTT | ACC | AAT | ATG | TTT | GCC | ACC | TGG | TCT | CCT | 6672 |
| Ile | Thr | Ala | Ser | Ser | Tyr | Phe | Thr | Asn | Met | Phe | Ala | Thr | Trp | Ser | Pro | |
| | 2210 | | | | | 2215 | | | | | 2220 | | | | | |
| TCA | AAA | GCT | CGA | CTT | CAC | CTC | CAA | GGG | AGG | AGT | AAT | GCC | TGG | AGA | CCT | 6720 |
| Ser | Lys | Ala | Arg | Leu | His | Leu | Gln | Gly | Arg | Ser | Asn | Ala | Trp | Arg | Pro | |
| 2225 | | | | | 2230 | | | | | 2235 | | | | | 2240 | |
| CAG | GTG | AAT | AAT | CCA | AAA | GAG | TGG | CTG | CAA | GTG | GAC | TTC | CAG | AAG | ACA | 6768 |
| Gln | Val | Asn | Asn | Pro | Lys | Glu | Trp | Leu | Gln | Val | Asp | Phe | Gln | Lys | Thr | |
| | | | | 2245 | | | | | 2250 | | | | | 2255 | | |
| ATG | AAA | GTC | ACA | GGA | GTA | ACT | ACT | CAG | GGA | GTA | AAA | TCT | CTG | CTT | ACC | 6816 |
| Met | Lys | Val | Thr | Gly | Val | Thr | Thr | Gln | Gly | Val | Lys | Ser | Leu | Leu | Thr | |
| | | | 2260 | | | | | 2265 | | | | | 2270 | | | |

```
AGC ATG TAT GTG AAG GAG TTC CTC ATC TCC AGC AGT CAA GAT GGC CAT      6864
Ser Met Tyr Val Lys Glu Phe Leu Ile Ser Ser Ser Gln Asp Gly His
    2275            2280                2285

CAG TGG ACT CTC TTT TTT CAG AAT GGC AAA GTA AAG GTT TTT CAG GGA      6912
Gln Trp Thr Leu Phe Phe Gln Asn Gly Lys Val Lys Val Phe Gln Gly
2290            2295                2300

AAT CAA GAC TCC TTC ACA CCT GTG GTG AAC TCT CTA GAC CCA CCG TTA      6960
Asn Gln Asp Ser Phe Thr Pro Val Val Asn Ser Leu Asp Pro Pro Leu
2305            2310                2315                2320

CTG ACT CGC TAC CTT CGA ATT CAC CCC CAG AGT TGG GTG CAC CAG ATT      7008
Leu Thr Arg Tyr Leu Arg Ile His Pro Gln Ser Trp Val His Gln Ile
            2325                2330                2335

GCC CTG AGG ATG GAG GTT CTG GGC TGC GAG GCA CAG GAC CTC TAC          7053
Ala Leu Arg Met Glu Val Leu Gly Cys Glu Ala Gln Asp Leu Tyr
            2340            2345                2350

TGA                                                                   7056
```

( 2 ) INFORMATION FOR SEQ ID NO:2:

( i ) SEQUENCE CHARACTERISTICS:
        ( A ) LENGTH: 2351 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Ile Glu Leu Ser Thr Cys Phe Phe Leu Cys Leu Leu Arg Phe
1               5               10              15

Cys Phe Ser Ala Thr Arg Arg Tyr Tyr Leu Gly Ala Val Glu Leu Ser
            20              25              30

Trp Asp Tyr Met Gln Ser Asp Leu Gly Glu Leu Pro Val Asp Ala Arg
        35              40              45

Phe Pro Pro Arg Val Pro Lys Ser Phe Pro Phe Asn Thr Ser Val Val
    50              55              60

Tyr Lys Lys Thr Leu Phe Val Glu Phe Thr Val His Leu Phe Asn Ile
65              70              75                          80

Ala Lys Pro Arg Pro Pro Trp Met Gly Leu Leu Gly Pro Thr Ile Gln
            85              90              95

Ala Glu Val Tyr Asp Thr Val Val Ile Thr Leu Lys Asn Met Ala Ser
            100             105             110

His Pro Val Ser Leu His Ala Val Gly Val Ser Tyr Trp Lys Ala Ser
            115             120             125

Glu Gly Ala Glu Tyr Asp Asp Gln Thr Ser Gln Arg Glu Lys Glu Asp
130             135             140

Asp Lys Val Phe Pro Gly Gly Ser His Thr Tyr Val Trp Gln Val Leu
145             150             155             160

Lys Glu Asn Gly Pro Met Ala Ser Asp Pro Leu Cys Leu Thr Tyr Ser
            165             170             175

Tyr Leu Ser His Val Asp Leu Val Lys Asp Leu Asn Ser Gly Leu Ile
            180             185             190

Gly Ala Leu Leu Val Cys Arg Glu Gly Ser Leu Ala Lys Glu Lys Thr
            195             200             205

Gln Thr Leu His Lys Phe Ile Leu Leu Phe Ala Val Phe Asp Glu Gly
210             215             220

Lys Ser Trp His Ser Glu Thr Lys Asn Ser Leu Met Gln Asp Arg Asp
225             230             235             240
```

-continued

| | | | | | | | | | | | | | | |
|---|---|---|---|---|---|---|---|---|---|---|---|---|---|---|
| Ala | Ala | Ser | Ala | Arg 245 | Ala | Trp | Pro | Lys | Met 250 | His | Thr | Val | Asn | Gly Tyr 255 |
| Val | Asn | Arg | Ser 260 | Leu | Pro | Gly | Leu | Ile 265 | Gly | Cys | His | Arg | Lys 270 | Ser Val |
| Tyr | Trp | His 275 | Val | Ile | Gly | Met | Gly 280 | Thr | Thr | Pro | Glu | Val 285 | His | Ser Ile |
| Phe | Leu 290 | Glu | Gly | His | Thr | Phe 295 | Leu | Val | Arg | Asn | His 300 | Arg | Gln | Ala Ser |
| Leu 305 | Glu | Ile | Ser | Pro | Ile 310 | Thr | Phe | Leu | Thr | Ala 315 | Gln | Thr | Leu | Leu Met 320 |
| Asp | Leu | Gly | Gln | Phe 325 | Leu | Leu | Phe | Cys | His 330 | Ile | Ser | Ser | His 335 | Gln His |
| Asp | Gly | Met | Glu 340 | Ala | Tyr | Val | Lys | Val 345 | Asp | Ser | Cys | Pro 350 | Glu | Glu Pro |
| Gln | Leu | Arg 355 | Met | Lys | Asn | Asn | Glu 360 | Glu | Ala | Glu | Asp | Tyr 365 | Asp | Asp Asp |
| Leu | Thr 370 | Asp | Ser | Glu | Met | Asp 375 | Val | Val | Arg | Phe | Asp 380 | Asp | Asp | Asn Ser |
| Pro 385 | Ser | Phe | Ile | Gln | Ile 390 | Arg | Ser | Val | Ala | Lys 395 | Lys | His | Pro | Lys Thr 400 |
| Trp | Val | His | Tyr | Ile 405 | Ala | Ala | Glu | Glu | Asp 410 | Trp | Asp | Tyr | Ala 415 | Pro |
| Leu | Val | Leu | Ala 420 | Pro | Asp | Asp | Arg | Ser 425 | Tyr | Lys | Ser | Gln 430 | Tyr | Leu Asn |
| Asn | Gly | Pro 435 | Gln | Arg | Ile | Gly | Arg 440 | Lys | Tyr | Lys | Lys | Val 445 | Arg | Phe Met |
| Ala | Tyr 450 | Thr | Asp | Glu | Thr | Phe 455 | Lys | Thr | Arg | Glu | Ala 460 | Ile | Gln | His Glu |
| Ser 465 | Gly | Ile | Leu | Gly | Pro 470 | Leu | Leu | Tyr | Gly | Glu 475 | Val | Gly | Asp | Thr Leu 480 |
| Leu | Ile | Ile | Phe | Lys 485 | Asn | Gln | Ala | Ser | Arg 490 | Pro | Tyr | Asn | Ile | Tyr Pro 495 |
| His | Gly | Ile | Thr 500 | Asp | Val | Arg | Pro | Leu 505 | Tyr | Ser | Arg | Arg | Leu 510 | Pro Lys |
| Gly | Val | Lys 515 | His | Leu | Lys | Asp | Phe 520 | Pro | Ile | Leu | Pro | Gly 525 | Glu | Ile Phe |
| Lys | Tyr 530 | Lys | Trp | Thr | Val | Thr 535 | Val | Glu | Asp | Gly | Pro 540 | Thr | Lys | Ser Asp |
| Pro 545 | Arg | Cys | Leu | Thr | Arg 550 | Tyr | Tyr | Ser | Ser | Phe 555 | Val | Asn | Met | Glu Arg 560 |
| Asp | Leu | Ala | Ser | Gly 565 | Leu | Ile | Gly | Pro | Leu 570 | Leu | Ile | Cys | Tyr | Lys Glu 575 |
| Ser | Val | Asp | Gln 580 | Arg | Gly | Asn | Gln | Ile 585 | Met | Ser | Asp | Lys 590 | Arg | Asn Val |
| Ile | Leu | Phe 595 | Ser | Val | Phe | Asp | Glu 600 | Asn | Arg | Ser | Trp | Tyr 605 | Leu | Thr Glu |
| Asn | Ile 610 | Gln | Arg | Phe | Leu | Pro 615 | Asn | Pro | Ala | Gly | Val 620 | Gln | Leu | Glu Asp |
| Pro 625 | Glu | Phe | Gln | Ala | Ser 630 | Asn | Ile | Met | His | Ser 635 | Ile | Asn | Gly | Tyr Val 640 |
| Phe | Asp | Ser | Leu | Gln 645 | Leu | Ser | Val | Cys | Leu 650 | His | Glu | Val | Ala | Tyr Trp 655 |
| Tyr | Ile | Leu | Ser | Ile 660 | Gly | Ala | Gln | Thr | Asp 665 | Phe | Leu | Ser | Val 670 | Phe Phe |

| | | | | | | | | | | | | | | |
|---|---|---|---|---|---|---|---|---|---|---|---|---|---|---|
| Ser | Gly | Tyr 675 | Thr | Phe | Lys | His | Met 680 | Val | Tyr | Glu | Asp 685 | Thr | Leu | Thr |
| Leu | Phe 690 | Pro | Phe | Ser | Gly 695 | Glu | Thr | Val | Phe | Met 700 | Ser | Met | Glu | Asn Pro |
| Gly 705 | Leu | Trp | Ile | Leu 710 | Gly | Cys | His | Asn | Ser 715 | Asp | Phe | Arg | Asn | Arg Gly 720 |
| Met | Thr | Ala | Leu | Leu 725 | Lys | Val | Ser | Ser | Cys 730 | Asp | Lys | Asn | Thr | Gly 735 Asp |
| Tyr | Tyr | Glu | Asp 740 | Ser | Tyr | Glu | Asp | Ile 745 | Ser | Ala | Tyr | Leu | Leu 750 | Ser Lys |
| Asn | Asn | Ala 755 | Ile | Glu | Pro | Arg | Ser 760 | Phe | Ser | Gln | Asn | Ser 765 | Arg | His Pro |
| Ser | Thr 770 | Arg | Gln | Lys | Gln | Phe 775 | Asn | Ala | Thr | Thr | Ile 780 | Pro | Glu | Asn Asp |
| Ile 785 | Glu | Lys | Thr | Asp | Pro 790 | Trp | Phe | Ala | His | Arg 795 | Thr | Pro | Met | Pro Lys 800 |
| Ile | Gln | Asn | Val | Ser 805 | Ser | Ser | Asp | Leu | Leu 810 | Met | Leu | Leu | Arg | Gln Ser 815 |
| Pro | Thr | Pro | His 820 | Gly | Leu | Ser | Leu | Ser 825 | Asp | Leu | Gln | Glu | Ala 830 | Lys Tyr |
| Glu | Thr | Phe 835 | Ser | Asp | Asp | Pro | Ser 840 | Pro | Gly | Ala | Ile | Asp 845 | Ser | Asn Asn |
| Ser | Leu 850 | Ser | Glu | Met | Thr | His 855 | Phe | Arg | Pro | Gln | Leu 860 | His | His | Ser Gly |
| Asp 865 | Met | Val | Phe | Thr | Pro 870 | Glu | Ser | Gly | Leu | Gln 875 | Leu | Arg | Leu | Asn Glu 880 |
| Lys | Leu | Gly | Thr | Thr 885 | Ala | Ala | Thr | Glu | Leu 890 | Lys | Lys | Leu | Asp | Phe Lys 895 |
| Val | Ser | Ser | Thr 900 | Ser | Asn | Asn | Leu | Ile 905 | Ser | Thr | Ile | Pro | Ser 910 | Asp Asn |
| Leu | Ala | Ala 915 | Gly | Thr | Asp | Asn | Thr 920 | Ser | Ser | Leu | Gly | Pro 925 | Pro | Ser Met |
| Pro | Val 930 | His | Tyr | Asp | Ser | Gln 935 | Leu | Asp | Thr | Thr | Leu 940 | Phe | Gly | Lys Lys |
| Ser 945 | Ser | Pro | Leu | Thr | Glu 950 | Ser | Gly | Gly | Pro | Leu 955 | Ser | Leu | Ser | Glu Glu 960 |
| Asn | Asn | Asp | Ser | Lys 965 | Leu | Leu | Glu | Ser | Gly 970 | Leu | Met | Asn | Ser | Gln Glu 975 |
| Ser | Ser | Trp | Gly 980 | Lys | Asn | Val | Ser | Ser 985 | Thr | Glu | Ser | Gly | Arg 990 | Leu Phe |
| Lys | Gly | Lys 995 | Arg | Ala | His | Gly | Pro 1000 | Ala | Leu | Leu | Thr | Lys 1005 | Asp | Asn Ala |
| Leu | Phe 1010 | Lys | Val | Ser | Ile | Ser 1015 | Leu | Leu | Lys | Thr | Asn 1020 | Lys | Thr | Ser Asn |
| Asn 1025 | Ser | Ala | Thr | Asn | Arg 1030 | Lys | Thr | His | Ile | Asp 1035 | Gly | Pro | Ser | Leu Leu 1040 |
| Ile | Glu | Asn | Ser | Pro 1045 | Ser | Val | Trp | Gln | Asn 1050 | Ile | Leu | Glu | Ser | Asp Thr 1055 |
| Glu | Phe | Lys | Lys 1060 | Val | Thr | Pro | Leu | Ile 1065 | His | Asp | Arg | Met | Leu 1070 | Met Asp |
| Lys | Asn | Ala 1075 | Thr | Ala | Leu | Arg | Leu 1080 | Asn | His | Met | Ser | Asn 1085 | Lys | Thr Thr |
| Ser | Ser | Lys | Asn | Met | Glu | Met | Val | Gln | Gln | Lys | Lys | Glu | Gly | Pro Ile |

|      |      |      |
|------|------|------|
| 1090 | 1095 | 1100 |

Pro Pro Asp Ala Gln Asn Pro Asp Met Ser Phe Phe Lys Met Leu Phe
1105                    1110                    1115                    1120

Leu Pro Glu Ser Ala Arg Trp Ile Gln Arg Thr His Gly Lys Asn Ser
             1125                    1130                    1135

Leu Asn Ser Gly Gln Gly Pro Ser Pro Lys Gln Leu Val Ser Leu Gly
             1140                    1145                    1150

Pro Glu Lys Ser Val Glu Gly Gln Asn Phe Leu Ser Glu Lys Asn Lys
             1155                    1160                    1165

Val Val Val Gly Lys Gly Glu Phe Thr Lys Asp Val Gly Leu Lys Glu
             1170                    1175                    1180

Met Val Phe Pro Ser Ser Arg Asn Leu Phe Leu Thr Asn Leu Asp Asn
1185                    1190                    1195                    1200

Leu His Glu Asn Asn Thr His Asn Gln Glu Lys Lys Ile Gln Glu Glu
             1205                    1210                    1215

Ile Glu Lys Lys Glu Thr Leu Ile Gln Glu Asn Val Val Leu Pro Gln
             1220                    1225                    1230

Ile His Thr Val Thr Gly Thr Lys Asn Phe Met Lys Asn Leu Phe Leu
             1235                    1240                    1245

Leu Ser Thr Arg Gln Asn Val Glu Gly Ser Tyr Glu Gly Ala Tyr Ala
             1250                    1255                    1260

Pro Val Leu Gln Asp Phe Arg Ser Leu Asn Asp Ser Thr Asn Arg Thr
1265                    1270                    1275                    1280

Lys Lys His Thr Ala His Phe Ser Lys Lys Gly Glu Glu Glu Asn Leu
             1285                    1290                    1295

Glu Gly Leu Gly Asn Gln Thr Lys Gln Ile Val Glu Lys Tyr Ala Cys
             1300                    1305                    1310

Thr Thr Arg Ile Ser Pro Asn Thr Ser Gln Gln Asn Phe Val Thr Gln
             1315                    1320                    1325

Arg Ser Lys Arg Ala Leu Lys Gln Phe Arg Leu Pro Leu Glu Glu Thr
             1330                    1335                    1340

Glu Leu Glu Lys Arg Ile Ile Val Asp Asp Thr Ser Thr Gln Trp Ser
1345                    1350                    1355                    1360

Lys Asn Met Lys His Leu Thr Pro Ser Thr Leu Thr Gln Ile Asp Tyr
             1365                    1370                    1375

Asn Glu Lys Glu Lys Gly Ala Ile Thr Gln Ser Pro Leu Ser Asp Cys
             1380                    1385                    1390

Leu Thr Arg Ser His Ser Ile Pro Gln Ala Asn Arg Ser Pro Leu Pro
             1395                    1400                    1405

Ile Ala Lys Val Ser Ser Phe Pro Ser Ile Arg Pro Ile Tyr Leu Thr
             1410                    1415                    1420

Arg Val Leu Phe Gln Asp Asn Ser Ser His Leu Pro Ala Ala Ser Tyr
1425                    1430                    1435                    1440

Arg Lys Lys Asp Ser Gly Val Gln Glu Ser Ser His Phe Leu Gln Gly
             1445                    1450                    1455

Ala Lys Lys Asn Asn Leu Ser Leu Ala Ile Leu Thr Leu Glu Met Thr
             1460                    1465                    1470

Gly Asp Gln Arg Glu Val Gly Ser Leu Gly Thr Ser Ala Thr Asn Ser
             1475                    1480                    1485

Val Thr Tyr Lys Lys Val Glu Asn Thr Val Leu Pro Lys Pro Asp Leu
             1490                    1495                    1500

Pro Lys Thr Ser Gly Lys Val Glu Leu Leu Pro Lys Val His Ile Tyr
1505                    1510                    1515                    1520

| | | | | | | | | | | | | | | |
|---|---|---|---|---|---|---|---|---|---|---|---|---|---|---|
|Gln|Lys|Asp|Leu|Phe|Pro|Thr|Glu|Thr|Ser|Asn|Gly|Ser|Pro|Gly|His|
| | | | |1525| | | |1530| | | |1535| | |
|Leu|Asp|Leu|Val|Glu|Gly|Ser|Leu|Leu|Gln|Gly|Thr|Glu|Gly|Ala|Ile|
| | | |1540| | | |1545| | | |1550| | | |
|Lys|Trp|Asn|Glu|Ala|Asn|Arg|Pro|Gly|Lys|Val|Pro|Phe|Leu|Arg|Val|
| |1555| | | | |1560| | | | |1565| | | |
|Ala|Thr|Glu|Ser|Ser|Ala|Lys|Thr|Pro|Ser|Lys|Leu|Leu|Asp|Pro|Leu|
| |1570| | | | |1575| | | |1580| | | | |
|Ala|Trp|Asp|Asn|His|Tyr|Gly|Thr|Gln|Ile|Pro|Lys|Glu|Glu|Trp|Lys|
|1585| | | |1590| | | |1595| | | | |1600| |
|Ser|Gln|Glu|Lys|Ser|Pro|Glu|Lys|Thr|Ala|Phe|Lys|Lys|Lys|Asp|Thr|
| | | | |1605| | | |1610| | | |1615| | |
|Ile|Leu|Ser|Leu|Asn|Ala|Cys|Glu|Ser|Asn|His|Ala|Ile|Ala|Ala|Ile|
| | | |1620| | | |1625| | | |1630| | | |
|Asn|Glu|Gly|Gln|Asn|Lys|Pro|Glu|Ile|Glu|Val|Thr|Trp|Ala|Lys|Gln|
| | | |1635| | | |1640| | | |1645| | | |
|Gly|Arg|Thr|Glu|Arg|Leu|Cys|Ser|Gln|Asn|Pro|Pro|Val|Leu|Lys|Arg|
| |1650| | | |1655| | | | |1660| | | | |
|His|Gln|Arg|Glu|Ile|Thr|Arg|Thr|Thr|Leu|Gln|Ser|Asp|Gln|Glu|Glu|
|1665| | | |1670| | | |1675| | | |1680| | |
|Ile|Asp|Tyr|Asp|Asp|Thr|Ile|Ser|Val|Glu|Met|Lys|Lys|Glu|Asp|Phe|
| | | |1685| | | |1690| | | |1695| | | |
|Asp|Ile|Tyr|Asp|Glu|Asp|Glu|Asn|Gln|Ser|Pro|Arg|Ser|Phe|Gln|Lys|
| | |1700| | | |1705| | | | |1710| | | |
|Lys|Thr|Arg|His|Tyr|Phe|Ile|Ala|Ala|Val|Glu|Arg|Leu|Trp|Asp|Tyr|
| | |1715| | | |1720| | | | |1725| | | |
|Gly|Met|Ser|Ser|Ser|Pro|His|Val|Leu|Arg|Asn|Arg|Ala|Gln|Ser|Gly|
| |1730| | | | |1735| | | |1740| | | | |
|Ser|Val|Pro|Gln|Phe|Lys|Lys|Val|Val|Phe|Gln|Glu|Phe|Thr|Asp|Gly|
|1745| | | |1750| | | |1755| | | |1760| | |
|Ser|Phe|Thr|Gln|Pro|Leu|Tyr|Arg|Gly|Glu|Leu|Asn|Glu|His|Leu|Gly|
| | | |1765| | | |1770| | | | |1775| | |
|Leu|Leu|Gly|Pro|Tyr|Ile|Arg|Ala|Glu|Val|Glu|Asp|Asn|Ile|Met|Val|
| | |1780| | | |1785| | | | |1790| | | |
|Thr|Phe|Arg|Asn|Gln|Ala|Ser|Arg|Pro|Tyr|Ser|Phe|Tyr|Ser|Ser|Leu|
| |1795| | | | |1800| | | | |1805| | | |
|Ile|Ser|Tyr|Glu|Glu|Asp|Gln|Arg|Gln|Gly|Ala|Glu|Pro|Arg|Lys|Asn|
|1810| | | | |1815| | | | |1820| | | | |
|Phe|Val|Lys|Pro|Asn|Glu|Thr|Lys|Thr|Tyr|Phe|Trp|Lys|Val|Gln|His|
|1825| | | |1830| | | |1835| | | | |1840| |
|His|Met|Ala|Pro|Thr|Lys|Asp|Glu|Phe|Asp|Cys|Lys|Ala|Trp|Ala|Tyr|
| | | |1845| | | |1850| | | |1855| | | |
|Phe|Ser|Asp|Val|Asp|Leu|Glu|Lys|Asp|Val|His|Ser|Gly|Leu|Ile|Gly|
| | | |1860| | | |1865| | | |1870| | | |
|Pro|Leu|Leu|Val|Cys|His|Thr|Asn|Thr|Leu|Asn|Pro|Ala|His|Gly|Arg|
| | | |1875| | | |1880| | | |1885| | | |
|Gln|Val|Thr|Val|Gln|Glu|Phe|Ala|Leu|Phe|Phe|Thr|Ile|Phe|Asp|Glu|
| |1890| | | |1895| | | | |1900| | | | |
|Thr|Lys|Ser|Trp|Tyr|Phe|Thr|Glu|Asn|Met|Glu|Arg|Asn|Cys|Arg|Ala|
|1905| | | |1910| | | |1915| | | | |1920| |
|Pro|Cys|Asn|Ile|Gln|Met|Glu|Asp|Pro|Thr|Phe|Lys|Glu|Asn|Tyr|Arg|
| | | |1925| | | |1930| | | |1935| | | |
|Phe|His|Ala|Ile|Asn|Gly|Tyr|Ile|Met|Asp|Thr|Leu|Pro|Gly|Leu|Val|
| | |1940| | | |1945| | | | |1950| | | |

Met Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr Val
    1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
                2005                2010                2015

Val Glu Cys Leu Ile Gly Glu His Leu His Ala Gly Met Ser Thr Leu
                2020                2025                2030

Phe Leu Val Tyr Ser Asn Lys Cys Gln Thr Pro Leu Gly Met Ala Ser
            2035                2040                2045

Gly His Ile Arg Asp Phe Gln Ile Thr Ala Ser Gly Gln Tyr Gly Gln
        2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
            2085                2090                2095

Pro Met Ile Ile His Gly Ile Lys Thr Gln Gly Ala Arg Gln Lys Phe
        2100                2105                2110

Ser Ser Leu Tyr Ile Ser Gln Phe Ile Ile Met Tyr Ser Leu Asp Gly
        2115                2120                2125

Lys Lys Trp Gln Thr Tyr Arg Gly Asn Ser Thr Gly Thr Leu Met Val
        2130                2135                2140

Phe Phe Gly Asn Val Asp Ser Ser Gly Ile Lys His Asn Ile Phe Asn
2145                2150                2155                2160

Pro Pro Ile Ile Ala Arg Tyr Ile Arg Leu His Pro Thr His Tyr Ser
            2165                2170                2175

Ile Arg Ser Thr Leu Arg Met Glu Leu Met Gly Cys Asp Leu Asn Ser
        2180                2185                2190

Cys Ser Met Pro Leu Gly Met Glu Ser Lys Ala Ile Ser Asp Ala Gln
        2195                2200                2205

Ile Thr Ala Ser Ser Tyr Phe Thr Asn Met Phe Ala Thr Trp Ser Pro
2210                2215                2220

Ser Lys Ala Arg Leu His Leu Gln Gly Arg Ser Asn Ala Trp Arg Pro
2225            2230                2235                2240

Gln Val Asn Asn Pro Lys Glu Trp Leu Gln Val Asp Phe Gln Lys Thr
            2245                2250                2255

Met Lys Val Thr Gly Val Thr Thr Gln Gly Val Lys Ser Leu Leu Thr
            2260                2265                2270

Ser Met Tyr Val Lys Glu Phe Leu Ile Ser Ser Ser Gln Asp Gly His
        2275                2280                2285

Gln Trp Thr Leu Phe Phe Gln Asn Gly Lys Val Lys Val Phe Gln Gly
2290                2295                2300

Asn Gln Asp Ser Phe Thr Pro Val Val Asn Ser Leu Asp Pro Pro Leu
2305            2310                2315                2320

Leu Thr Arg Tyr Leu Arg Ile His Pro Gln Ser Trp Val His Gln Ile
            2325                2330                2335

Ala Leu Arg Met Glu Val Leu Gly Cys Glu Ala Gln Asp Leu Tyr
            2340                2345                2350

( 2 ) INFORMATION FOR SEQ ID NO:3:

( i ) SEQUENCE CHARACTERISTICS:

(A) LENGTH: 1623 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
 (A) NAME/KEY: CDS
 (B) LOCATION: 1..1623

(xi) SEQUENCE DESCRIPTION: SEQ ID NO:3:

| | | | | | | | | | | | | | | | | |
|---|---|---|---|---|---|---|---|---|---|---|---|---|---|---|---|---|
| TTT | GCG | GTG | TTT | GAT | GAA | GGG | AAA | AGT | TGG | CAC | TCA | GCA | AGA | AAT | GAC | 48 |
| Phe | Ala | Val | Phe | Asp | Glu | Gly | Lys | Ser | Trp | His | Ser | Ala | Arg | Asn | Asp | |
| 1 | | | | 5 | | | | | 10 | | | | | 15 | | |
| TCC | TGG | ACA | CGG | GCC | ATG | GAT | CCC | GCA | CCT | GCC | AGG | GCC | CAG | CCT | GCA | 96 |
| Ser | Trp | Thr | Arg | Ala | Met | Asp | Pro | Ala | Pro | Ala | Arg | Ala | Gln | Pro | Ala | |
| | | | 20 | | | | | 25 | | | | | 30 | | | |
| ATG | CAC | ACA | GTC | AAT | GGC | TAT | GTC | AAC | AGG | TCT | CTG | CCA | GGT | CTG | ATC | 144 |
| Met | His | Thr | Val | Asn | Gly | Tyr | Val | Asn | Arg | Ser | Leu | Pro | Gly | Leu | Ile | |
| | | | 35 | | | | 40 | | | | | 45 | | | | |
| GGA | TGT | CAT | AAG | AAA | TCA | GTC | TAC | TGG | CAC | GTG | ATT | GGA | ATG | GGC | ACC | 192 |
| Gly | Cys | His | Lys | Lys | Ser | Val | Tyr | Trp | His | Val | Ile | Gly | Met | Gly | Thr | |
| | | 50 | | | | | 55 | | | | | 60 | | | | |
| AGC | CCG | GAA | GTG | CAC | TCC | ATT | TTT | CTT | GAA | GGC | CAC | ACG | TTT | CTC | GTG | 240 |
| Ser | Pro | Glu | Val | His | Ser | Ile | Phe | Leu | Glu | Gly | His | Thr | Phe | Leu | Val | |
| 65 | | | | | 70 | | | | | 75 | | | | | 80 | |
| AGG | CAC | CAT | CGC | CAG | GCT | TCC | TTG | GAG | ATC | TCG | CCA | CTA | ACT | TTC | CTC | 288 |
| Arg | His | His | Arg | Gln | Ala | Ser | Leu | Glu | Ile | Ser | Pro | Leu | Thr | Phe | Leu | |
| | | | | 85 | | | | | 90 | | | | | 95 | | |
| ACT | GCT | CAG | ACA | TTC | CTG | ATG | GAC | CTT | GGC | CAG | TTC | CTA | CTG | TTT | TGT | 336 |
| Thr | Ala | Gln | Thr | Phe | Leu | Met | Asp | Leu | Gly | Gln | Phe | Leu | Leu | Phe | Cys | |
| | | | 100 | | | | | 105 | | | | | 110 | | | |
| CAT | ATC | TCT | TCC | CAC | CAC | CAT | GGT | GGC | ATG | GAG | GCT | CAC | GTC | AGA | GTA | 384 |
| His | Ile | Ser | Ser | His | His | His | Gly | Gly | Met | Glu | Ala | His | Val | Arg | Val | |
| | | 115 | | | | | 120 | | | | | 125 | | | | |
| GAA | AGC | TGC | GCC | GAG | GAG | CCC | CAG | CTG | CGG | AGG | AAA | GCT | GAT | GAA | GAG | 432 |
| Glu | Ser | Cys | Ala | Glu | Glu | Pro | Gln | Leu | Arg | Arg | Lys | Ala | Asp | Glu | Glu | |
| | 130 | | | | | 135 | | | | | 140 | | | | | |
| GAA | GAT | TAT | GAT | GAC | AAT | TTG | TAC | GAC | TCG | GAC | ATG | GAC | GTG | GTC | CGG | 480 |
| Glu | Asp | Tyr | Asp | Asp | Asn | Leu | Tyr | Asp | Ser | Asp | Met | Asp | Val | Val | Arg | |
| 145 | | | | | 150 | | | | | 155 | | | | | 160 | |
| CTC | GAT | GGT | GAC | GAC | GTG | TCT | CCC | TTT | ATC | CAA | ATC | CGC | TCG | GTT | GCC | 528 |
| Leu | Asp | Gly | Asp | Asp | Val | Ser | Pro | Phe | Ile | Gln | Ile | Arg | Ser | Val | Ala | |
| | | | | 165 | | | | | 170 | | | | | 175 | | |
| AAG | AAG | CAT | CCC | AAA | ACC | TGG | GTG | CAC | TAC | ATC | TCT | GCA | GAG | GAG | GAG | 576 |
| Lys | Lys | His | Pro | Lys | Thr | Trp | Val | His | Tyr | Ile | Ser | Ala | Glu | Glu | Glu | |
| | | | 180 | | | | | 185 | | | | | 190 | | | |
| GAC | TGG | GAC | TAC | GCC | CCC | GCG | GTC | CCC | AGC | CCC | AGT | GAC | AGA | AGT | TAT | 624 |
| Asp | Trp | Asp | Tyr | Ala | Pro | Ala | Val | Pro | Ser | Pro | Ser | Asp | Arg | Ser | Tyr | |
| | | 195 | | | | | 200 | | | | | 205 | | | | |
| AAA | AGT | CTC | TAC | TTG | AAC | AGT | GGT | CCT | CAG | CGA | ATT | GGT | AGG | AAA | TAC | 672 |
| Lys | Ser | Leu | Tyr | Leu | Asn | Ser | Gly | Pro | Gln | Arg | Ile | Gly | Arg | Lys | Tyr | |
| | 210 | | | | | 215 | | | | | 220 | | | | | |
| AAA | AAA | GCT | CGA | TTC | GTC | GCT | TAC | ACG | GAT | GTA | ACA | TTT | AAG | ACT | CGT | 720 |
| Lys | Lys | Ala | Arg | Phe | Val | Ala | Tyr | Thr | Asp | Val | Thr | Phe | Lys | Thr | Arg | |
| 225 | | | | | 230 | | | | | 235 | | | | | 240 | |
| AAA | GCT | ATT | CCG | TAT | GAA | TCA | GGA | ATC | CTG | GGA | CCT | TTA | CTT | TAT | GGA | 768 |
| Lys | Ala | Ile | Pro | Tyr | Glu | Ser | Gly | Ile | Leu | Gly | Pro | Leu | Leu | Tyr | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| GAA | GTT | GGA | GAC | ACA | CTT | TTG | ATT | ATA | TTT | AAG | AAT | AAA | GCG | AGC | CGA | 816 |
| Glu | Val | Gly | Asp | Thr | Leu | Leu | Ile | Ile | Phe | Lys | Asn | Lys | Ala | Ser | Arg | |
| | | | 260 | | | | | 265 | | | | | 270 | | | |
| CCA | TAT | AAC | ATC | TAC | CCT | CAT | GGA | ATC | ACT | GAT | GTC | AGC | GCT | TTG | CAC | 864 |
| Pro | Tyr | Asn | Ile | Tyr | Pro | His | Gly | Ile | Thr | Asp | Val | Ser | Ala | Leu | His | |
| | | 275 | | | | | 280 | | | | | 285 | | | | |
| CCA | GGG | AGA | CTT | CTA | AAA | GGT | TGG | AAA | CAT | TTG | AAA | GAC | ATG | CCA | ATT | 912 |
| Pro | Gly | Arg | Leu | Leu | Lys | Gly | Trp | Lys | His | Leu | Lys | Asp | Met | Pro | Ile | |
| | | 290 | | | | | 295 | | | | | 300 | | | | |
| CTG | CCA | GGA | GAG | ACT | TTC | AAG | TAT | AAA | TGG | ACA | GTG | ACT | GTG | GAA | GAT | 960 |
| Leu | Pro | Gly | Glu | Thr | Phe | Lys | Tyr | Lys | Trp | Thr | Val | Thr | Val | Glu | Asp | |
| 305 | | | | | 310 | | | | | 315 | | | | | 320 | |
| GGG | CCA | ACC | AAG | TCC | GAT | CCT | CGG | TGC | CTG | ACC | CGC | TAC | TAC | TCG | AGC | 1008 |
| Gly | Pro | Thr | Lys | Ser | Asp | Pro | Arg | Cys | Leu | Thr | Arg | Tyr | Tyr | Ser | Ser | |
| | | | | 325 | | | | | 330 | | | | | 335 | | |
| TCC | ATT | AAT | CTA | GAG | AAA | GAT | CTG | GCT | TCG | GGA | CTC | ATT | GGC | CCT | CTC | 1056 |
| Ser | Ile | Asn | Leu | Glu | Lys | Asp | Leu | Ala | Ser | Gly | Leu | Ile | Gly | Pro | Leu | |
| | | | 340 | | | | | 345 | | | | | 350 | | | |
| CTC | ATC | TGC | TAC | AAA | GAA | TCT | GTA | GAC | CAA | AGA | GGA | AAC | CAG | ATG | ATG | 1104 |
| Leu | Ile | Cys | Tyr | Lys | Glu | Ser | Val | Asp | Gln | Arg | Gly | Asn | Gln | Met | Met | |
| | | 355 | | | | | 360 | | | | | 365 | | | | |
| TCA | GAC | AAG | AGA | AAC | GTC | ATC | CTG | TTT | TCT | GTA | TTC | GAT | GAG | AAT | CAA | 1152 |
| Ser | Asp | Lys | Arg | Asn | Val | Ile | Leu | Phe | Ser | Val | Phe | Asp | Glu | Asn | Gln | |
| 370 | | | | | 375 | | | | | 380 | | | | | | |
| AGC | TGG | TAC | CTC | GCA | GAG | AAT | ATT | CAG | CGC | TTC | CTC | CCC | AAT | CCG | GAT | 1200 |
| Ser | Trp | Tyr | Leu | Ala | Glu | Asn | Ile | Gln | Arg | Phe | Leu | Pro | Asn | Pro | Asp | |
| 385 | | | | | 390 | | | | | 395 | | | | | 400 | |
| GGA | TTA | CAG | CCC | CAG | GAT | CCA | GAG | TTC | CAA | GCT | TCT | AAC | ATC | ATG | CAC | 1248 |
| Gly | Leu | Gln | Pro | Gln | Asp | Pro | Glu | Phe | Gln | Ala | Ser | Asn | Ile | Met | His | |
| | | | 405 | | | | | 410 | | | | | 415 | | | |
| AGC | ATC | AAT | GGC | TAT | GTT | TTT | GAT | AGC | TTG | CAG | CTG | TCG | GTT | TGT | TTG | 1296 |
| Ser | Ile | Asn | Gly | Tyr | Val | Phe | Asp | Ser | Leu | Gln | Leu | Ser | Val | Cys | Leu | |
| | | | 420 | | | | | 425 | | | | | 430 | | | |
| CAC | GAG | GTG | GCA | TAC | TGG | TAC | ATT | CTA | AGT | GTT | GGA | GCA | CAG | ACG | GAC | 1344 |
| His | Glu | Val | Ala | Tyr | Trp | Tyr | Ile | Leu | Ser | Val | Gly | Ala | Gln | Thr | Asp | |
| | | 435 | | | | | 440 | | | | | 445 | | | | |
| TTC | CTC | TCC | GTC | TTC | TTC | TCT | GGC | TAC | ACC | TTC | AAA | CAC | AAA | ATG | GTC | 1392 |
| Phe | Leu | Ser | Val | Phe | Phe | Ser | Gly | Tyr | Thr | Phe | Lys | His | Lys | Met | Val | |
| | 450 | | | | | 455 | | | | | 460 | | | | | |
| TAT | GAA | GAC | ACA | CTC | ACC | CTG | TTC | CCC | TTC | TCA | GGA | GAA | ACG | GTC | TTC | 1440 |
| Tyr | Glu | Asp | Thr | Leu | Thr | Leu | Phe | Pro | Phe | Ser | Gly | Glu | Thr | Val | Phe | |
| 465 | | | | | 470 | | | | | 475 | | | | | 480 | |
| ATG | TCA | ATG | GAA | AAC | CCA | GGT | CTC | TGG | GTC | CTA | GGG | TGC | CAC | AAC | TCA | 1488 |
| Met | Ser | Met | Glu | Asn | Pro | Gly | Leu | Trp | Val | Leu | Gly | Cys | His | Asn | Ser | |
| | | | | 485 | | | | | 490 | | | | | 495 | | |
| GAC | TTG | CGG | AAC | AGA | GGG | ATG | ACA | GCC | TTA | CTG | AAG | GTG | TAT | AGT | TGT | 1536 |
| Asp | Leu | Arg | Asn | Arg | Gly | Met | Thr | Ala | Leu | Leu | Lys | Val | Tyr | Ser | Cys | |
| | | | 500 | | | | | 505 | | | | | 510 | | | |
| GAC | AGG | GAC | ATT | GGT | GAT | TAT | TAT | GAC | AAC | ACT | TAT | GAA | GAT | ATT | CCA | 1584 |
| Asp | Arg | Asp | Ile | Gly | Asp | Tyr | Tyr | Asp | Asn | Thr | Tyr | Glu | Asp | Ile | Pro | |
| | | 515 | | | | | 520 | | | | | 525 | | | | |
| GGC | TTC | TTG | CTG | AGT | GGA | AAG | AAT | GTC | ATT | GAA | CCC | AGA | | | | 1623 |
| Gly | Phe | Leu | Leu | Ser | Gly | Lys | Asn | Val | Ile | Glu | Pro | Arg | | | | |
| | | 530 | | | | | 535 | | | | | 540 | | | | |

( 2 ) INFORMATION FOR SEQ ID NO:4:

( i ) SEQUENCE CHARACTERISTICS:
        ( A ) LENGTH: 541 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Phe Ala Val Phe Asp Glu Gly Lys Ser Trp His Ser Ala Arg Asn Asp
 1               5                  10                  15

Ser Trp Thr Arg Ala Met Asp Pro Ala Pro Ala Arg Ala Gln Pro Ala
             20                  25                  30

Met His Thr Val Asn Gly Tyr Val Asn Arg Ser Leu Pro Gly Leu Ile
         35                  40                  45

Gly Cys His Lys Lys Ser Val Tyr Trp His Val Ile Gly Met Gly Thr
     50                  55                  60

Ser Pro Glu Val His Ser Ile Phe Leu Glu Gly His Thr Phe Leu Val
 65                  70                  75                  80

Arg His His Arg Gln Ala Ser Leu Glu Ile Ser Pro Leu Thr Phe Leu
                 85                  90                  95

Thr Ala Gln Thr Phe Leu Met Asp Gly Gln Phe Leu Leu Phe Cys
             100                 105                 110

His Ile Ser Ser His His His Gly Gly Met Glu Ala His Val Arg Val
         115                 120                 125

Glu Ser Cys Ala Glu Glu Pro Gln Leu Arg Arg Lys Ala Asp Glu Glu
     130                 135                 140

Glu Asp Tyr Asp Asp Asn Leu Tyr Asp Ser Asp Met Asp Val Val Arg
145                 150                 155                 160

Leu Asp Gly Asp Asp Val Ser Pro Phe Ile Gln Ile Arg Ser Val Ala
                 165                 170                 175

Lys Lys His Pro Lys Thr Trp Val His Tyr Ile Ser Ala Glu Glu Glu
             180                 185                 190

Asp Trp Asp Tyr Ala Pro Ala Val Pro Ser Pro Ser Asp Arg Ser Tyr
         195                 200                 205

Lys Ser Leu Tyr Leu Asn Ser Gly Pro Gln Arg Ile Gly Arg Lys Tyr
     210                 215                 220

Lys Lys Ala Arg Phe Val Ala Tyr Thr Asp Val Thr Phe Lys Thr Arg
225                 230                 235                 240

Lys Ala Ile Pro Tyr Glu Ser Gly Ile Leu Gly Pro Leu Leu Tyr Gly
                 245                 250                 255

Glu Val Gly Asp Thr Leu Leu Ile Ile Phe Lys Asn Lys Ala Ser Arg
             260                 265                 270

Pro Tyr Asn Ile Tyr Pro His Gly Ile Thr Asp Val Ser Ala Leu His
         275                 280                 285

Pro Gly Arg Leu Leu Lys Gly Trp Lys His Leu Lys Asp Met Pro Ile
     290                 295                 300

Leu Pro Gly Glu Thr Phe Lys Tyr Lys Trp Thr Val Thr Val Glu Asp
305                 310                 315                 320

Gly Pro Thr Lys Ser Asp Pro Arg Cys Leu Thr Arg Tyr Tyr Ser Ser
                 325                 330                 335

Ser Ile Asn Leu Glu Lys Asp Leu Ala Ser Gly Leu Ile Gly Pro Leu
             340                 345                 350

Leu Ile Cys Tyr Lys Glu Ser Val Asp Gln Arg Gly Asn Gln Met Met
         355                 360                 365

Ser Asp Lys Arg Asn Val Ile Leu Phe Ser Val Phe Asp Glu Asn Gln
     370                 375                 380

Ser Trp Tyr Leu Ala Glu Asn Ile Gln Arg Phe Leu Pro Asn Pro Asp
385                 390                 395                 400
```

```
Gly  Leu  Gln  Pro  Gln  Asp  Pro  Glu  Phe  Gln  Ala  Ser  Asn  Ile  Met  His
               405                      410                      415

Ser  Ile  Asn  Gly  Tyr  Val  Phe  Asp  Ser  Leu  Gln  Leu  Ser  Val  Cys  Leu
               420                      425                      430

His  Glu  Val  Ala  Tyr  Trp  Tyr  Ile  Leu  Ser  Val  Gly  Ala  Gln  Thr  Asp
               435                      440                      445

Phe  Leu  Ser  Val  Phe  Phe  Ser  Gly  Tyr  Thr  Phe  Lys  His  Lys  Met  Val
     450                           455                      460

Tyr  Glu  Asp  Thr  Leu  Thr  Leu  Phe  Pro  Phe  Ser  Gly  Glu  Thr  Val  Phe
465                      470                      475                      480

Met  Ser  Met  Glu  Asn  Pro  Gly  Leu  Trp  Val  Leu  Gly  Cys  His  Asn  Ser
               485                      490                      495

Asp  Leu  Arg  Asn  Arg  Gly  Met  Thr  Ala  Leu  Leu  Lys  Val  Tyr  Ser  Cys
               500                      505                      510

Asp  Arg  Asp  Ile  Gly  Asp  Tyr  Tyr  Asp  Asn  Thr  Tyr  Glu  Asp  Ile  Pro
               515                      520                      525

Gly  Phe  Leu  Leu  Ser  Gly  Lys  Asn  Val  Ile  Glu  Pro  Arg
     530                      535                      540
```

( 2 ) INFORMATION FOR SEQ ID NO:5:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

GCAAAGCTTC TGGGTTCA                                                    18

( 2 ) INFORMATION FOR SEQ ID NO:6:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Leu  Leu  Phe  Ala  Val  Phe  Asp  Glu
1                   5
```

( 2 ) INFORMATION FOR SEQ ID NO:7:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GGAATCTTYG CNGTNTTYGA YGA                                              23

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Tyr Ile Ala Ala Glu Glu
 1               5
```

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

```
TAYATBGCNG CNGARGA                                                    17
```

( 2 ) INFORMATION FOR SEQ ID NO:10:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

```
GTAAAAACAA TGCCATTGAA ACGCGTAGCT TCTCCCAGAA TTC                       43
```

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

```
TTGAAACGCG TAGCT                                                      15
```

( 2 ) INFORMATION FOR SEQ ID NO:12:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

CCTTCCTTTA TCCAAACGCG TTCAGTTGCC AAGAAGCATC C 41

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

CCAAACGCGT TCAGT 15

( 2 ) INFORMATION FOR SEQ ID NO:14:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GCCATTGAAC CAAGATGATG AGTCGACAGC TTCTCCCAGA ATTC 44

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

GATGATGAGT CGACA 15

( 2 ) INFORMATION FOR SEQ ID NO:16:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GTCCAGAGGA ACCCCAAACG CGTATGAAAA ATAATGAAG                    39

( 2 ) INFORMATION FOR SEQ ID NO:17:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

CCAAACGCGT ATGAA                    15

( 2 ) INFORMATION FOR SEQ ID NO:18:

( i ) SEQUENCE CHARACTERISTICS:
                ( A ) LENGTH: 44 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GCCACAACTC AGACTTTCGG ACGCGTGGCA TGACCGCCTT ACTG                    44

( 2 ) INFORMATION FOR SEQ ID NO:19:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

TTTCGGACGC GTGGC                    15

( 2 ) INFORMATION FOR SEQ ID NO:20:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

GAATTCGTCG ACTGATGAAC GTGGTTCAAT GACATT    36

( 2 ) INFORMATION FOR SEQ ID NO:21:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

TCTCCCTTTA TCCAAACGCG TTCGGTTGCC AAGAAG    36

( 2 ) INFORMATION FOR SEQ ID NO:22:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

TCTCCCTTTA TCCAAACGCG TTCGGTTGCC AAGAAG    36

( 2 ) INFORMATION FOR SEQ ID NO:23:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

CTGGGCAAAG CTACGCGTTT CAATGACATT CTTTCC    36

( 2 ) INFORMATION FOR SEQ ID NO:24:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

TCAGACTTGC GGACGCGTGG GATGACA    27

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

CTGGGAGAAG CTACGCGTTT CAATGACATT        30

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

GAGGAGCCCC AGACGCGTAG GAAAGCTGAT        30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:27:

CTTGGCAACC GAACGCGTTT GGATAAAGGG        30

CHIMERIC PROCOAGULANT PROTEINS

CROSS-REFERENCE TO RELATED APPLICATIONS

The present application is a continuation-in-part of U.S. Ser. No. 07/976,086, filed Nov. 13, 1992, now abandoned.

FIELD OF THE INVENTION

The present invention relates generally to chimeric procoagulant proteins, to porcine factor VIII nucleotide sequences, and to hybrid sequences encoding human/porcine chimeric factor VIII-type activity.

BACKGROUND OF THE INVENTION

Factor VIII is a protein involved in clotting blood and plays a critical role in hemostasis. The lack of factor VIII leads to the bleeding disorder hemophilia A. Hemostasis is maintained by an intricate and complex regulation of both coagulation and anti-coagulation pathways in the blood. The clotting cascade begins when cell damage activates the enzyme factor XII and ends when soluble fibrinogen is converted into fibrin by thrombin. The pathway involves the interaction of many proteolytic enzymes, e.g., factors XII, XI, IX, X and prothrombin, as well as numerous co-factors such as factors VIII and V. Once coagulation is initiated, the response is amplified by a cascade of protease activation steps that occur on the surface of endothelial cells and platelets. At each step an inactive protein is converted into a protease which in turn activates the next protein in the pathway. The cascade includes both positive-feedback and negative-feedback loops. The clotting pathway eventually leads to the formation of insoluble fibrin which, together with platelets, obscures blood flow at the site of tissue damage.

Certain steps of the pathway are accelerated by co-factors, such as factors VIII and V. Approximately 85 percent of hemophiliacs lack factor VIII; the remainder lack factor IX. Thrombin not only activates factors VIII and V, but it also can deactivate them, i.e., by activating protein C. The exact mechanisms by which the levels and activities of active factor VIII are controlled are still not completely understood.

Traditionally, hemophiliacs were treated with transfusions of whole blood. More recently, treatment has been with preparations of factor VIII concentrates derived from human plasma. However, the use of plasma-derived product exposes hemophilia patients to the possible risk of virus-transmissible diseases such as hepatitis and AIDS. Costly purification schemes to reduce this risk increases treatment costs. With increases in costs and limited availability of plasma-derived factor VIII, patients are treated episodically on a demand basis rather than prophylactically. Moreover, factor VIII typically exhibits limited stability after activation with thrombin, necessitating administration of large amounts of protein during a bleeding episode. Recombinantly produced factor VIII has substantial advantages over plasma-derived factor VIII in terms of purity and safety, as well as increased availability. Procoagulant proteins with enhanced stability are desirable to minimize the amount of protein infused into a patient during a bleeding episode. Accordingly, much research effort has been directed towards the development of recombinantly produced factor VIII.

In light of the known immunogenicity of plasma-derived factor VIII, one of the goals in developing new recombinant forms of factor VIII for use as a therapeutic agent is the development of products that do not induce an immune response. Approximately 15 percent of all hemophiliacs develop an immune response to factor VIII replacement therapy at some time during their lives. The resultant antibody production causes inhibition of subsequently infused factor VIII products and creates a difficult therapeutic situation for the patient. Attempts have been made, therefore, to develop recombinant forms of factor VIII that are modified in ways that reduce or eliminate such an immune response. It is not a priori possible, however, to predict in advance whether newly developed recombinant forms also result in the generation of new epitopes that, although absent from natural factor VIII preparations will themselves generate undesirable antibody responses.

Other goals in developing new, more stable recombinant forms of factor VIII include the introduction of specific mutations into factor VIII to gain an understanding of specific requirements for factor VIII activity, as well as the specific requirements for thrombin activation and subsequent inactivation of factor VIII. Because of the complex subunit structure and labile nature of factor VIII, and of its activated derivatives, study of the structure-function relationship has been difficult.

The domain, structure, and processing of factor VIII is set forth in detail in Kaufman, Nature 342:207(1989). The parent single chain precursor is 2351 amino acids long and has a domainal sequence of:

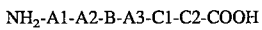

NH$_2$-A1-A2-B-A3-C1-C2-COOH

The full-length nucleotide sequence and corresponding amino acid sequence is set forth in SEQ ID NO: 1 and 2.

Upon secretion, a portion of the B domain is removed to generate an amino terminal-derived heavy chain (200 kD) and a carboxyl terminal-derived light chain (80 kD). The heavy chain is: NH$_2$-A1-A2-B and the light chain is: A3-C1-C2-COOH. There is a metal ion-dependent association between the two chains. In plasma, factor VIII circulates as an inactive co-factor which requires cleavage by thrombin, or by factor Xa, for activation; to subsequently inactivate the active form, proteolytic cleavage occurs at residue 336 by activated protein C or factor Xa. Activation is associated with cleavages between the A1 and A2 domains (position 372), between the A2 and B domains (position 740), and between the B and A3 domains (position 1689). The thrombin-activated form is referred to as factor VIIIa$_{IIA}$ and was believed to be a heterodimer with a subunit composition of A1/A3-C1-C2. Recently, Lollar et al., J. Biol. Chem. 266:12481 (1991); Fay, et al., J. Biol. Chem 266:8957 (1991); and Pittman, et al. Blood 79:389 (1992) presented evidence suggesting that human thrombin-activated VIII is heterotrimeric, i.e., A1/A2/A3-C1-C2.

Both human and porcine factor VIIIa$_{IIA}$ are unstable at physiological concentration and pH. However, porcine factor VIII has been found to be indefinitely stable at concentrations greater than 0.2 μM, at pH 6.0; in contrast, human factor VIIIa$_{IIA}$ loses activity under these in vitro conditions. However, subjecting the thrombin activated human factor VIII to Mono S chromatography at pH 5.0 increases the activity 10 fold and the active fraction contains greater concentrations of the A2 domain. For both human and porcine factor VIIIa$_{IIA}$, it has been suggested that dissociation of the A2 subunit is responsible for the loss of activity under the in vitro conditions selected (Lollar et al., supra.)

However, no in vivo studies have been performed to ascertain whether the association/dissociation of the A2 subunit has any affect on the in vivo blood clotting activity of factor VIII.

DNA sequences for human factor VIII are known, as are expression methods. Toole, et al., Nature 312:312 (1984); Wood, et al., Nature 312:330; Vehar, et al., Nature 312:337 (1984) and WO 87/04187; WO 88/08035; and WO 88/03558. In addition, human factor VIII analogs have been developed to better understand the specific structural requirements for factor VIII activability, inactivatibility, and in vivo efficacy. Included among the features to be optimized are simplified preparation, ease of administration, stability, improved clearance/distribution characteristics, reduced immunogenicity, and prolonged half-life. Available analogs have modified the factor VIII structure such that part or all of the B domain has been deleted [U.S. Pat. No. 4,868,112] and/or specific amino acid positions are modified to reduce factor VIII susceptibility to cleavage at one or more sites [PCT/US87/01299 (WO87/07144)]. In addition, attempts have been made to replace the factor VIII B domain sequence with the B domain sequence of factor V, another cofactor involved in the coagulation cascade [U.S. Pat. No. 5,004,803].

In contrast to human factor VIII, elucidation of the complete nucleic acid sequence for porcine factor VIII has been hampered for many years. Partial amino acid information for porcine factor VIII was described in Church, et al., *Proc. Natl. Acad. Sci.* 81:6934 (1984) for an internal 98-residue segment; a 26-residue segment from the $NH_2$ terminus and a 35-residue segment from the $NH_2$ terminus of a 35-kD thrombin activation peptide. The actual sequence information disclosed was only of those porcine factor VIII sequences corresponding to the N-terminal sequence of the porcine light chain having homology to two structurally related proteins, i.e., coagulation factor V and ceruloplasmin. The 26-residue segment and 98-residue internal sequence were not correctly located. Data presented, infra, and those described by Toole, et al., Nature 312:312 (1984), demonstrate that the sequence assignment by Church, et al., *Proc. Natl. Acad. Sci.* 81:6934 (1984) was incorrect. Subsequently, Toole, et al., Nature 312:342 (1984) provided limited N-terminal amino acid sequence analysis of cleavage fragments of porcine factor VIII. This information proved unsuitable for designing probes useful in cloning porcine factor VIII cDNA in that the resultant probes were too highly degenerate and insufficiently specific to detect porcine factor VIII cDNA. Several years later, Toole, et al., *Proc. Natl. Acad. Sci. USA* 83:5939 (1986), reported a high degree of divergence of amino acid sequence between porcine and human B domains of the factor VIII; accordingly, the human sequence proved unsuitable for designing probes to clone porcine factor VIII cDNA.

To date no one has been successful in determining the full length sequence for porcine factor VIII. Without such information it has been impossible to determine which structural features, if any, may play a role in porcine factor VIII's increased stability. Moreover, without such information it has been impossible to construct hybrid, or chimeric, factor VIII molecules having increased stability and specific activity, as well as chimeric forms that are immunologically distinct and which may be useful to treat those patients that have developed antibodies to human factor VIII. Accordingly, there continues to exist a need for further structural information for porcine factor VIII to design factor VIII analogs having improved stability and specific activity.

BRIEF SUMMARY

The present invention provides novel purified and isolated nucleic acid sequences encoding porcine factor VIII coagulant activity, provides novel purified and isolated nucleic acid sequences encoding human/porcine chimeric factor VIII activity, and provides novel purified and isolated nucleic acid sequences encoding human factor VIII analogs. Specifically provided is the nucleic acid sequence encoding porcine factor VIII activity and comprising the sequence substantially as set forth in SEQ ID NO:3. A recombinant porcine clone containing the nucleotide sequence set forth in SEQ ID NO:3 and designated por302, is on deposit with the American Type Culture Collection under the accession number ATCC 69387. SEQ ID NO:4 also provides the corresponding amino acid sequence. Presently preferred chimeric forms include those where various domains of the human factor VIII have been replaced, in whole or in part, by analogous porcine factor VIII domains and include, for example, chimeric forms where the A1 and/or A1 domains, in whole or in part, of the human factor VIII sequence have been replaced, in whole or in part, by the A1 and/or A2 domains of porcine factor VIII. Specifically provided are chimetic factor VIII sequences comprising the A1, A2, A3, B, C1 and C2 human domains of the sequence as set forth in SEQ ID NO:1, where the A1 and/or A2 domains, as well as other segments, such as the regions corresponding to amino acid numbers 336–372, 336–740, 372–740, 700–740, and combinations of these regions have been replaced in whole or in part with porcine factor VIII sequences, as set forth in SEQ ID NOS:3 and 4. Other preferred embodiments include chimeric factor VIII nucleic acid sequences where part or all of the B domain is deleted, and/or specific amino acid positions are modified, for example, such that normally protease labile sites are resistance to proteolysis, e.g., by thrombin or activated Protein C. Other chimeric forms include those where the nucleic acid sequence is substantially duplicative of a nucleic acid sequence selected from (a) and (b), wherein (a) is one or more members selected from the group consisting of human factor VIII domains A1, A2, B, A3, C1 and C2, and (b) is one or more members selected from the group consisting of porcine factor VIII domains A1, A2, B, A3, C1 and C2; and more specifically: (i) substantially duplicative of nucleotide sequences present in human domains A1, B, A3, C1 and C2 and porcine domain A2; (ii) substantially duplicative of nucleotide sequences present in human domains B, A3, C1 and C2 and porcine domains A1 and A2; (iii) substantially duplicative of nucleotide sequences present in human domains A1, A3, C1 and C2 and porcine A2; or (iv) substantially duplicative of nucleotide sequences present in human domains A3, C1 and C2 and porcine domains A1 and A2, as well as other segments, such as the regions corresponding to human amino acid numbers 336–372, 336–740, 372–740, 700–740 and combinations thereof.

In a further embodiment, the invention comprises the expression products of the nucleic acid sequences of the invention, as well as activated forms of these expression products. In addition, the present invention contemplates porcine factor VIII nucleic acid sequences encoding individual domains, which, when expressed, can be added back to the expression products of human factor VIII nucleic acid sequences, optionally having the corresponding domains deleted. In other words, functional factor VIII activity may be generated from single expression vectors comprising the sequences encoding one or more of the various domains, or, alternatively the activity can be generated from one or more expression vectors contained in one or more cell lines, each of which express their respective domain(s), which domain(s), when added back to each other, generate factor VIII clotting activity.

Alternate nucleic acid forms, such as genomic DNA, cDNA, and DNA prepared by partial or total chemical synthesis from nucleotides, as well as DNA with deletions or mutations, are also within the contemplation of the invention, such as the B domain deletion and cleavage site mutants referred to, supra. Also provided are novel messenger RNA (mRNA) sequences corresponding to these DNA sequences.

Association of nucleic acid sequences provided by the invention with homologous or heterologous species expression control sequences, such as promoters, operators, regulators, and the like, allows for in vivo and in vitro transcription to form mRNA which, in turn, is susceptible to translation to provide novel factor VIII hybrid proteins and related poly- and oligopeptides in large quantities. In a presently preferred expression system of the invention, factor VIII encoding sequences are operatively associated with a regulatory promoter sequence allowing for transcription and translation in a mammalian cell to provide, e.g., factor VIII having clotting activity.

The incorporation of these sequences into prokaryotic and eukaryotic host cells by standard transformation and transfection processes, potentially involving suitable viral and circular DNA plasmid vectors, is also within the contemplation of the invention and is expected to provide useful factor VIII in quantities greatly in excess of those attainable from plasma. The use of mammalian host cells provides for such post-translational modifications, e.g., truncation, glycosylation, tyrosine, serine, or threonine phosphorylation, as may be made to confer optimal biological activity on the expression products of the invention. Methods are provided for the production of the porcine factor VIII activity and of the chimeric human/porcine factor VIII activity in host cells or cell-free transcription/translation systems.

The novel protein products of the invention include those having the primary structural conformation, i.e., amino acid sequence, of the factor VIII hybrids, as well as hybrids assembled to be substantially duplicative of the hybrid nucleic acid sequences and having factor VIII coagulant activity. Preferred hybrids are those having enhanced activity and stability. Synthetic polypeptides can be manufactured according to standard synthetic methods. Also provided by the invention are novel pharmaceutical compositions and methods for treatment of hemophilia patients comprising administration of the novel factor VIII hybrids.

DESCRIPTION OF SEQ ID NOS. AND FIGURE

Other aspects and advantages of the present invention will be apparent upon consideration of the following detailed description hereof which includes numerous illustrative examples of the practice of the invention, with reference being made to the following Sequence Identification Numbers and Figure:

SEQ ID NOS: 1 and 2 provide, respectively, the 7,057 base pair nucleotide sequence and the deduced amino acid sequence for human factor VIII;

SEQ ID NOS:3 and 4 provide, respectively, the 1,623 base pair nucleotide sequence and deduced amino acid sequence for porcine factor VIII. It is presently believed that approximately 1 to 414–519 encodes the A1 domain and approximately 414–519 to 1623 encodes the A2 domain, with the acidic region at approximately 414–519.

FIG. 1 provides a comparison of the human and porcine factor VIII amino acid sequence with respect to the A2 and partial A1 domains, corresponding to amino acid residues 199 to 740 of the human amino acid sequence and corresponding to amino acid residues 1 to 541 of the porcine amino acid sequence. The numbers of the human sequence represent residue numbers beginning with residue 1 of the mature protein. Numbers for the porcine sequence represent an arbitrary numbering system as set forth in SEQ ID NO: 4. The sequences depicted in FIG. 1 are also set forth in SEQ ID NOS:2 and 4, supra.

FIG. 2 provides a schematic representation of the overall organization of the human factor VIII domains.

DETAILED DESCRIPTION

Factor VIII activity, as used herein, means one or more polypeptide(s) or proteins demonstrating procoagulant activity in a clotting assay and includes human polypeptides, porcine polypeptides, and human/porcine hybrid polypeptides, and human polypeptides together with porcine polypeptides. As used herein, the term "polypeptides" includes not only full length protein molecules but also fragments thereof which, by themselves or with other fragments, generate factor VIII procoagulant activity in a clotting assay. "Activated" factor VIII, as used herein, means factor VIII activity that has been treated with thrombin. A "hybrid factor VIII activity" is a term meant to include those molecules having domains selected from both human factor VIII sequences and porcine factor VIII sequences and is sometimes designated "human/porcine factor VIII activity". The domains comprising the "hybrid" or "chimeric" factor VIII activity may, but need not, be the expression product of one vector; rather, the domains can be separately and individually expressed from separate vectors and in separate cell systems. As used herein, the term "a sequence substantially corresponding to the sequence" of a SEQ ID NO. is meant to encompass those sequences which hybridize to the sequence of the SEQ ID NO. under stringent conditions as well as those which would hybridize but for the redundancy of the genetic code and which result in expression products having the specified activity. Stringent conditions are generally 0.2×SSC at 65° C. The term "substantially duplicative" is meant to include those sequences which, though they may not be identical to those set forth in the SEQ ID NO., still result in expression product, proteins, and/or synthetic polypeptides that have factor VIII activity in a standard clotting assay.

As used herein, the terms "domains" and "subunits" may be used interchangeably to refer to approximate regions of factor VIII in either human or porcine factor VIII. In human factor VIII, these domains correspond approximately to those set forth in Table I below. The terms "corresponding domain" and "corresponding subunits" include those regions of human factor VIII and porcine factor VIII having cognizable amino acid homology to each other, irrespective of the actual amino acid numbering system used. As is appreciated by one skilled in the art, these boundary designations are only approximate.

TABLE I

| Amino acid residue number at domain boundaries | | |
| --- | --- | --- |
| Domain | 5' Border | 3' Border |
| A1 | 1 | 329–336–372 |
| Heavy chain acidic domain | 336 | 372 |
| A2 | 336–372–377 | 710–740 |
| B | 710–740 | 1648–1689 |

TABLE I-continued

Amino acid residue number at domain boundaries

| Domain | 5' Border | 3' Border |
| --- | --- | --- |
| Light chain acidic domain | 1649 | 1689 |
| A3 | 1648–1689 | 2019 |
| C1 | 2020 | 2172 |
| C2 | 2173 | 2332 |

The approximate correspondence of certain human/porcine amino acid sequence designations is set forth in Table II.

TABLE II

Corresponding Human/Porcine Amino Acid Residue Numbers

| Human | Porcine |
| --- | --- |
| 336 | 138 |
| 372 | 174 |
| 700 | 501 |
| 740 | 541 |

As used herein, the terms "hybrid", "chimera", and "chimeric" may be used interchangeably to include factor VIII nuclueic acid sequences, amino acid sequences, expression products, and proteins comprising human and porcine factor VIII sequences. The term "analog" may also be used to include these chimeric/hybrid factor VIII forms, as well as B domain deletion forms and cleavage site mutants.

As used herein the terms co-transfection, co-expression, and co-cultivation are meant to include processes where the relevant nucleic acid sequences encoding the "domains" may be on a single or on a separate transfection or expression vector(s), and/or may be in one or more cell lines, and/or may be in one or more cultures, and/or may have one or more separate cultures mixed. In other words, at least the following five modes are possibilities: i) one cell type, one plasmid (having both human and porcine nucleic acid sequences); ii) one cell type, two plasmid types; iii) two cell types, one with a human plasmid, one with a porcine plasmid; iv) two cultures, each with one of two cell types (either a human plasmid or porcine plasmid) and v) mixing the conditioned medium of iv) and then purifying the factor VIII activity. Additional permutations of the foregoing are also possible as is evident to one skilled in the art. Co-transfection and co-expression may employ one or more domain sequences from porcine and/or from human factor VIII, or may employ domains having deletions from and/or cleavage site mutations in porcine and/or human factor VIII, to yield procoagulant activity.

The following examples illustrate practice of the invention. These examples are for illustrative purposes only and are not intended in any way to limit the scope of the invention claimed. Example 1 describes the preparation of human factor VIII nucleic acid sequences; Example 2 relates to the cloning of the porcine factor VIII gene; Example 3 describes the construction of chimeric human/porcine factor VIII and the transformation of mammalian cell lines to express chimeric human/porcine factor VIII; Example 4 describes pharmaceutical compositions and methods of use of chimeric human/porcine factor VIII.

EXAMPLE 1

PREPARATION OF HUMAN FACTOR VIII cDNA

Preparation of human factor VIII cDNA has been set forth in detail, e.g., U.S. Pat. No. 4,757,006 issued Jul. 12, 1988 and in Toole et al., Nature 312:312 (1984). A recombinant clone containing the nucleotide sequence depicted in SEQ ID NO: 1, designated as pSP64-VIII, is on deposit at the American Type Culture Collection under Accession Number ATCC 39812.

To minimize inconvenience in shuffling sequences between different vectors in subsequent Examples below, the mutagenesis of factor VIII cDNAs in those Examples was performed directly in the expression plasmid. Generally, the approach taken for mutagenesis was derived from the procedure of Morinaga et al, Bio/Technology 636 (July 1984) with conventional modifications. This approach is facilitated by the construction of plasmids which have convenient unique restriction sites in the factor VIII expression plasmid.

The following describes one such construction of a factor VIII expression plasmid which has unique Eco RV, HpaI, Cla I and Xba I restriction sites. Plasmid pMT2 DNA was prepared by conventional methods, e.g., by EcoRI digestion of pMT2-VWF, which has been deposited with the American Type Culture Collection under Accession number ATCC 67122. EcoRI digestion excises the cDNA insert present in pMT2-VWF, yielding pMT2 in linear form which can be ligated and used to transform Escherichia Coli HB 101 or DH-5 to ampicillin resistance. pMT2VIII was then constructed by digesting pMT2 with Eco RV and XbaI, treating the digested DNA with Klenow fragment of DNA polymerase I, and ligating Cla linkers (NEBiolabs, CATCGATG). This removed bases 2171 to 2421 starting from the Hind III site near the SV40 origin of replication and enhancer sequences of pMT2 (the ClaI derivative of pMT2). The factor VIII cDNA was excised from pSP64 VIII with SalI and blunted with T4 DNA polymerase, and EcoRI adapters added (AATrCCTCGAGAGCT). The EcoRI-adapted factor VIII eDNA was then ligated into the EcoRI site of the ClaI derivative of pMT2, designated pMT2CLA-VIII. The linker encodes for a internal Xho I, resulting in Xho I restriction sites flanking the factor VIII coding region. The unique 3' Sat I site was reconstructed by ligation of the 4648 bp Kpn I- Cla I fragment from the factor VIII expression plasmid D₂XRCVIII-4 (D₂XRCVIII-4 contains the full length factor VIII cDNA in the pXMT2 version of pMT2). The Xba I site at the 3' end of the cDNA derived from the SP64 polylinker was deleted by digestion with Xba I and treatment with the Klenow fragment of DNA polymerase I (followed by ligation and transformation) to the 7468 bp KpnI-ClaI fragment from pMT2 Cla VIII. The resultant plasmid is called pMT2-VIII is used in Example 3 below.

EXAMPLE 2

CLONING OF PORCINE FACTOR VIII

Previous attempts to clone porcine factor VIII were unsuccessful for a variety of reasons as described, supra. Generally, these unsuccessful attempts stemmed from the fact that the porcine factor VIII nucleotide sequence is significantly different from the human sequence thus making isolation of porcine using the human cDNA as a probe impossible.

A partial genomic clone for the porcine factor VIII B domain was obtained as described in U.S. Pat. No. 4,757, 006 supra. and included an intron connected to another exon presumed to be in the A2 domain. An oligonucleotide probe corresponding to the thrombin cleavage site at the carboxyl terminus of porcine factor VIII A2 domain was designed corresponding to the following sequence:

GCAAAGCTTCTGGGTICA    SEQ. ID NO:5

This sequence (P831) was derived from a porcine genomic clone that contains the protein sequence Glu Pro Arg Ser Ala Leu and corresponds to amino acids 738–743 of the human protein.

This probe, in combination with degenerate oligonucleotide probes made against various sequences in the A1 domain of human factor VIII, was used to amplify (as detailed below) the corresponding sequences for porcine factor VIII. The majority of the degenerate oligonucleotides used were unsuccessful in isolating the porcine sequence. This was due to the fact that the porcine sequence diverges significantly from the human sequence in many regions. Examples of sequences successfully used to isolate a porcine fragment are P857 which codes for the amino acid sequence:

Leu Leu Phe Ala Vat Phe Asp Glu    SEQ ID NO:6 and contains the degenerate sequence:

GGAATCTTYGCNGTNTTYGAYGA    SEQ ID NO:7 and P854 which codes for the sequence:

Tyr Ile Ala Ala Glu Glu    SEQ ID NO:8 and contains the sequence:

TAYATBGCNGCNGARGA.    SEQ ID NO:9

The actual amplification was as follows:

RNA was prepared from porcine liver and converted to complementary DNA using reverse transcriptase according to established protocols (*Molecular Cloning, A Laboratory Manual*. Sambrook J., E. Fritch and T. Maniatis). The resulting cDNA was subsequently used in a PCR reaction in the presence of a 5-prime oligonucleotide (e.g., P854) and a 3-prime oligonucleotide (e.g., P831). Upon 25 cycles of amplification (using Taq polymerase or Vent thermostable DNA polymerase), the products obtained were analyzed on an agarose gel. DNA bands of the expected size were isolated from the gel and inserted into a standard cloning vector pBSKS by first blunting with Klenow and then ligating with SmaI digested pBSKS in the presence of T4 DNA ligase. The ligation reaction was transformed into *E. coli* and colonies containing the inserted DNA were identified using restriction analysis of purified plasmids. Subsequently, sequence analysis was performed using the dideoxy chain termination method. The results are set forth in SEQ ID NO:3 which presents the 1623 base pair nucleotide sequence.

FIG. 1 provides a comparison of the human and porcine factor VIII amino acid sequence with respect to the A2 and partial A1 domains, corresponding to amino acid residues 199 to 740 of the human amino acid sequence and corresponding to amino acid residues 1 to 541 of the porcine amino acid sequence. The numbers of the human sequence represent residue numbers beginning with residue 1 of the mature protein. Numbers for the porcine sequence represent an arbitrary numbering system as set forth in SEQ ID NO: 4. The sequences depicted in FIG. 1 are also set forth in SEQ ID NOS:2 and 4, supra.

The transformed host cells, E. coli DH5 cells, transformed with porcine factor VIII, were designated por302 and deposited with the American Type Culture Collection (ATCC) on Aug. 17, 1993 and accorded Accession No. 69387.

At one point it was believed that porcine factor VIII did not contain sequences homologous to exon 13 of the human A2 subunit. In other words, the region spanning 617 through 685, present in human factor VIII, appeared to be absent from porcine factor VIII. Surprisingly, it has now been found that independent clones that were subsequently isolated do indeed contain sequences corresponding to exon 13 of human factor VIII. In addition, although certain portions of the porcine sequence were found to be homologous to the human protein sequence, there were significant differences in other specific regions. These differences were localized to specific regions, for example the acidic regions of the porcine and human A2 domains, i.e., amino acids 138 to 174 of porcine which corresponds to amino acids 336 to 372 of human (FIG. 1). It is postulated that the acidic region of human factor VIII plays a role in the function of the activated factor VIII molecule. The differences encoded in the porcine sequence, particularly in the regions corresponding to 336 to 740 of the human, play a role in the increased activity and in-vivo stability of porcine factor VIII.

The full length porcine factor VIII cDNA is estimated to be at least 7 kB in length. Having discovered the sequence of porcine factor VIII A1/A2 domains as described above, it was now possible to construct a highly specific probe to specifically isolate the remaining sequence of the porcine factor VIII cDNA. Also, it is now possible to construct human/porcine factor VIII chimera as is set forth in Example 3.

EXAMPLE 3

CONSTRUCTION AND EXPRESSION OF HUMAN/PORCINE FACTOR VIII CHIMERA

A. Construction Strategy

Having nucleotide sequence information for porcine factor VIII enabled the construction of human/porcine factor VIII chimera. The convenient exchange of domains between human and porcine FVIII was accomplished by introducing MluI sites into cDNAs encoding the respective factors. Because MluI does not happen to cut within either of the cDNAs, nor within the vector backbone, the unique introduced MluI sites facilitate the ability to exchange domains between the human FVIII and porcine FVIII cDNAs at will. If such a site is naturally present in alternative cDNAs or vectors such sites may be altered by site directed mutagenesis, if desired. Also, it should be understood that other unique restriction sites may be similarly introduced instead of MluI, or naturally occuring restriction sites may be abolished for the sake of convenience. The enzyme MluI recognizes the DNA sequence [5]'-ACGCGT- [3'], which happens to encode the amino acid sequence thr-arg. Fortuitously, this allows one to introduce MluI sites at particular cleavage sites, e.g. thrombin-cleavage sites, in which the amino-terminal residue is arg, without drastically altering the conformation of factor VIII at that site so as to not interfere with thrombin's capacity to cleave the resultant altered factor VIII.

It should be understood, of course, that all variant DNAs of this invention may be analogously produced by one skilled in the art by methods such as described herein for exemplary constructs.

The construction involved two steps. First, the appropriate domain sequence was deleted from human factor VIII, for example, by introducing restriction sites for the enzyme MluI at the boundaries of the sequence to be deleted using standard methods of site directed mutagenesis. Such techniques have also been used to modify a cDNA at specific sites, whether by replacing or deleting one or more bases. Such methods of mutagenesis include the M13 system of Zoller et al., *Nucleic Acids Res.* 10:6487–6500 (1982); *Methods Enzymol.* 100:468–500 (1983); and *DNA* 3:479–488 (1984), using single stranded DNA and the method of Morinaga et al., *Bio/technology*:636–639 (July 1984), using heteroduplexed DNA or using PCR mutagenesis.

Second, the corresponding sequence of porcine factor VIII (to be inserted into the modified human factor VIII) was constructed such that it contained MluI sites at its ends, for example, by PCR mutagenesis where the oligonucleotides used to amplify the corresponding porcine sequence incorporated the changes that result in MluI sites. The PCR product was digested with MluI and then inserted into human factor VIII containing a deletion flanked by MluI sites thereby enabling the insertion of the porcine sequence of interest. The hybrid constructed in this way was then expressed in an appropriate host, e.g., mammalian cells, and the resulting hybrid factor VIII molecule was analyzed for procoagulant activity.

Purification of DNA fragments was according to conventional techniques, such as those set forth in Maniatis et al., *Molecular Cloning, A Laboratory Manual* (Cold Spring Harbor Laboratory 1982) and *Proc. Natl. Acad. Sci.* 76:615–619 (1979), the disclosure of which is incorporated herein by reference. The purified DNA was then ligated using known methods to form the sequence encoding the hybrid procoagulant proteins of the present invention. When necessary or desirable, the ligation may be with an oligonucleotide that reseels the cut DNA and maintains the correct translational reading frame using standard ligation conditions.

B. Mutagenesis of Human and Porcine Factor VHI Sequences

Exemplary oligonucleotides used to generate restriction sites in the human and porcine factor VIII, as described, supra, are shown in Table III, below. References to human amino acid numbers are in "mutations" 1–10; reference to porcine amino acid numbers are in "mutations" 11–18; "names" are based on relative human amino acid number.

TABLE III

Exemplary Oligonucleotides

| Name | No. | SEQ ID NO: | Sequence | Mutation |
|---|---|---|---|---|
| FVIII 740 | 1. | 10 | 5'(GTA AAA ACA ATG CCA TTG AAA CGC GTA GCT TCT CCC AGA ATT C)3' | $^P739^R740 \rightarrow {}^T739^R740$ |
| Screen 740 | 2. | 11 | 5'(TTG AAA CGC GTA GCT)3' | *(1) |
| FVIII 372 | 3. | 12 | 5'(CCT TCC TTT ATC CAA ACG CGT TCA GTT GCC AAG AAG CAT CC | $^I371^R372 \rightarrow {}^T371^R372$ |
| Screen 372 | 4. | 13 | 5'(CCA AAC GCG TTC AGT)3' | *(3) |
| pHC | 5. | 14 | 5'(GCCATTGAACCAAGATGATGAG TCGACAGCTTCTCCCAGAATTC)3' | termination codons after $^R740$ |
| Screen pHC | 6. | 15 | 5'(GATGATGAGTCGACA)3' | *(8) |
| FVIII 336 | 7. | 16 | 5'(GTC CAG AGG AAC CCC AA ACG CGT ATC AAA AAT AAT GAA G)3' | $^L335^R336 \rightarrow {}^T335^R336$ |
| Screen 336 | 8. | 17 | 5'(CCA AAC GCG TAT GAA)3' | *(11) |
| FVIII 700 | 9. | 18 | 5'(GC CAC AAC TCA GAC TTT CGG ACG CGT GGC ATG ACC GCC TTA CTG)3' | $^N699^R700 \rightarrow {}^T699^R700$ |
| Screen 700 | 10. | 19 | 5'(TTT CGG ACG CGT GGC)3' | *(17) |
| P8A2 stop | 11. | 20 | 5'(GAATTCGTCGACTGATGA ACGTGGTTCAATGACATT)3' | Termination after $R_{541}$ |
| P8A2MluI55 | 12. | 21 | 5'(TCTCCCTTTATCCAAACGCGTT CGGTTGCCAAGAAG)3' | $P_{540}R_{541} \rightarrow T_{540}R_{541}$ |
| A2-372-5' | 13. | 22 | 5'(TCTCCCTTTATCCAAACGCGT TCGGTTGCCAAGAAG)3' | $I_{172}R_{173} \rightarrow T_{172}R_{173}$ |
| A2-740-3' | 14. | 23 | 5'(CTGGGCAAAGCTACGCGT TTCAATGACATTCTTTCC)3' | $P_{540}R_{541} \rightarrow T_{540}R_{541}$ |
| A2B-700-5' | 15. | 24 | 5'(TCAGACTTGCGGACGCGTGGGATGACA)3' | $N_{500}R_{501} \rightarrow T_{500}R_{501}$ |
| A2B-740-3' | 16. | 25 | 5'(CTGGGAGAAGCTACGCGTT TCAATGACATT)3' | $P_{540}R_{541} \rightarrow T_{540}R_{541}$ |
| A1A2-336-5' | 17 | 26 | 5'(GAGGAGCCCCAGACGCGT AGGAAAGCTGAT)3' | $R_{138}R_{139} \rightarrow T_{138}R_{139}$ |
| A1A2-372-3' | 18 | 27 | 5'(CTTGGCAACCGAACGCGT TTGGATAAAGGG)3' | $I_{172}R_{173} \rightarrow T_{172}R_{173}$ |

*Used for screening mutagenesis event effected with the oligonucleotide indicated in parentheses. Codons for replacement amino acids are underlined. As those skilled in this art will appreciate, oligonucleotides can be readily constructed for use in deleting one or more amino acids or for inserting a different (replacement) amino acid at a desired site by deleting one or more codons or substituting the codon for the desired amino acid in the oligonucleotide, respectively. Other mutagensesis oligonucleotides can be designed based on an approximately 20–50 nucleotide sequence spanning the desired site, with replacement or deletion of the original codon(s) one wishes to change.

Mutagenesis was performed with the following DNA preparations. Plasmid pMT2-VIII of Example 1 was linearized with ClaI, treated with calf intestinal phosphatase, and separated on a low melting temperature tris-acetate agarose gel. The band of linearized DNA was then extracted by absorption to silica dioxide and eluted in tris-EDTA, or by phenol extraction and ethanol precipitation. A second lot of pMT2-VIII was digested with KpnI-XhoI, KpnI-EcoRV or EcoRV-XbaI and the DNA fragments were separated by electrophoresis on a low melting temperature agarose gel and extracted as above. One µg of each of the appropriate plasmids was mixed and the volume was adjusted to 18 µl and 2.0 µl of 2N NaOH was added. The mixture was denatured at room temperature for 10 min, then neutralized with 180 µl of a solution which is 0.02N HCl and 0.1M Tris-HCl pH 8.0. Twenty picomoles of phosphorylated mutagenic oligonucleotide were added to 40 µl of the heteroduplex mixture. The mixture was placed in a 68° C. heat block for 90 min. After the incubation the mixture was allowed to slowly cool at room temperature. For each mutagenic reaction, 40 µl of the heteroduplex oligonucleotide mixture was used. The reactions were made 2 mM $MgCl_2$, 1 mM beta-mercaptoethanol, 400 µM ATP, 100 µM deoxynucleotide triphosphate, 3–4 units/µl of Klenow fragment of E. coli DNA polymerase I and 400 units/µl of T4 DNA ligase. The reactions were incubated for 10 minutes at room temperature, transferred to 16° C. and incubated overnight. The reaction was terminated by phenol-chloroform extraction and ethanol precipitation, and the resultant pellet was washed with 70% ethanol and re-suspended in 10 µl of sterile $H_2O$. DNA was then used to transform competent HB101 or DH-5 bacteria. The ampicillin resistant colonies were screened with $1 \times 10^6$ cpm/ml of a $^{32}$P-labeled screening oligonucleotide in 5×SSC, 0.1% SDS, 5×Denhardt's reagent, and 100 µg/ml denatured salmon sperm DNA. The filters were washed with 5×SSC, 0.1% SDS at a temperature 5 degrees below the calculated melting temperature of the oligonucleotide probe. DNA was prepared from positively hybridizing clones and analyzed initially by digestion with different restriction enzymes and agarose gel electrophoresis. DNA was transferred to nitrocellulose filters which were prepared and hybridized to the screening probes in order to ensure the mutagenic oligonucleotide was introduced into the correct fragment. DNA was then re-transformed into E. coli and ampicillin resistant colonies were screened for hybridization to the screening oligonucleotide. Final mutations were confirmed by DNA sequencing (e.g., Sanger et al., *Proc. Natl. Acad. Sci. USA* 74:5463–5467 (1977)).

Plasmid derivations were constructed as follows. Mutagenesis of the 90 kDa (amino acid 740) cleavage site in human factor VIII was performed by the gapped heteroduplex method as described above (Morinaga et al., *Bio/Technology* 84:636–639) using the KpnI-EcoRV 10.1 kb fragment from pMT2-VIII and the ClaI linearized pMT2-VIII DNA to produce gapped heteroduplexes. The mutagenic oligonucleotide was No. 1 in Table III and the screening oligonucleotide was the 15-mer No. 2 in Table III. The resultant mutant was verified to be correct by DNA sequencing (Sanger et al., *Proc. Natl. Acad. Sci. USA* 74:5463 (1977). The resultant DNA (p740 MluI) was prepared by banding to equilibrium in CsCl.

Mutagenesis of the 50 kDa (amino acid 372) cleavage site was performed by preparing a gapped heteroduplex using ClaI linearized pMT2-VIII DNA and the KpnI-XhoI fragment of pMT2-VIII. The mutagenic oligonucleotide was No. 3 in Table III and the screening oligonucleotide was No. 4 in Table III. The resultant mutant was verified to be correct by DNA sequencing as above. The resultant DNA (p372 MluI) was prepared CsCl banding and extensively characterized.

Mutagenesis of the residues at 335–336 was performed by preparing a gapped heteroduplex using ClaI linearized pMT2 VIII and the KpnI-XhoI fragment of pMT2-VIII. Mutagenic oligo 7 in Table III and screening oligonucleotide No. 8 in Table III. The resulting DNA p336 Mlu was prepared by CsCl banding and characterized by sequencing.

To generate the plasmid designated p700–740 MluI, a gapped heteroduplex of ClaI linearized pMT2-VIII and KpnI-EcoRV 10.1Kb fragment from p740MluI was prepared. The mutagenic oligonucleotide is No. 9 in Table III and the screening oligonucleotide is No. 10 in Table III. The resultant DNA was prepared by banding to equilibrium in CsCl and verified to be correct by DNA sequencing. ps C. Construction of Hybrids As explained, supra, the various regions of the sequences encoding factor VIII may be derived from either the porcine or the human factor VIII. The sequences can be on separate or on the same vector and can be contained within the same cell or not.

First is described the co-transfection of porcine and human factor VIII sequences on separate vectors. Second is described the construction of hybrid sequences where the porcine and human sequences are contained within one transfection vector.

1. Construction and Co-transfection of Porcine and Human Factor VHI Sequences On Separate Vectors The plasmid harboring a deletion of the A2 domain from human factor VIII was constructed by the addition of a unique MluI restriction site at nucleotides 1,168–1,173 and 2,272–2,277 (nucleotide 1 is the A of the initiation codon ATG). This mutation corresponds to the thrombin cleavage sites at arginines 372 and 740. The resulting plasmids were designated p372MluI and p740MluI, respectively. The A2 domain deletion was generated by ligation of the 4,973 bp MluI-ClaI fragment from p372MluI-Cla I 6,139-bp fragment from p740MluI. The ligated DNA was used to transform E. coli DH5 or HB101. The resulting plasmid, designated human ΔA2, has the human A2 domain deleted by juxtaposing arginine 372 to serine 741. Introduction of the MluI site at residue 372 changes an isoleucine at 371 to a threonine.

An A2 only (human as well as porcine) expression vector was constructed by first constructing an expression vector pHC, which directs the synthesis of the human heavy chain polypeptide. pHC was constructed by site directed mutagenesis using the gapped heteroduplex method using ClaI linearized pMT2-VIII DNA and the KpnI-ECORV 10.1Kb fragment from pMT2-VIII DNA to introduce two termination codons (TGATGA) and a Sal I restriction site immediately after arginine 740 (nucleotide 2,278) using the mutagenic oligonucleotide No. 5 in Table III and the screening oligonucleotide No. 6. The remainder of the factor VIII cDNA was deleted by Sal I digestion, ligation and transformation of E. coli DH5 to obtain pHC. The DNA was prepared by CsCl banding and sequenced. Oligonucleotides encoding for the factor VIII signal peptide containing a unique MluI site at the 3' end and a unique XhoI site at the 5' end were ligated to XhoI-MluI digested p372MluI. The resulting plasmid designated human ΔA1, has the A1 domain from amino acid 20 to 371 deleted. The human A1 alone expression plasmid was then constructed by digestion of pHC with KpnI and XhoI, ligation to KpnI-XhoI digested Δ A1. The resultant plasmid was designated human A2. To summarize, this plasmid has only the A2 domain of human factor VIII.

To facilitate subcloning the porcine A2 fragment, the oligonucleotide P8A2 stop (3') number 11 Table III and the oligonucleotide P8A2MluI55 (5') number 12 in Table III were used in a PCR reaction using Vent polymerase. Upon 25 cycles of amplification the product was obtained and analyzed on an agarose gel. The 3' oligonucleotide introduces two stop codons and a unique SalI restriction site. The porcine A2 expression plasmid was prepared by digestion of the human A2 expression plasmid with MluI and SalI and ligation to MluI-SalI digested PCR fragment encoding the porcine A2 domain, and transformation of E. coli DH5. The resultant DNA designated porA2 was prepared by banding to equilibrium in CsCl and sequenced.

2. Construction of and Transfection With Porcine/Human Hybrid Vectors

While the description provides for the insertion of porcine sequences into human, it will be appreciated by one skilled in the art that constructs resulting in factor VIII activity can also be generated by inserting human sequences into porcine sequences. The overall organization of the human factor VIII domains is schematically represented in FIG. 2.

TABLE IV

| Construct Designation | Region Replaced With Analogous Porcine Region |
|---|---|
| pHVIIIP 336-372 | 336-372 |
| pHVIIIP 700-740 | 700-740 |
| pHVIIIP 336-740 | 336-740 |
| pHVIIIP 372-740 | 372-740 |
| pHVIIIP 336-372/700-740 | 336-372/700-740 |

Each of the five hybrids set forth in Table IV above was constructed as follows:

1. To obtain the porcine acidic region, the oligonucleotide A1A2-336 5' number 17 and A1A2-372 3' number 18 Table III were used in a PCR reaction of por 302 using Vent polymerase. Upon 25 cycles of amplification, the product obtained was digested with MluI, separated on an agarose gel and purified. The factor VIII chimera harboring 138–174 (human porcine 336–372) was constructed by ligation of the MluI digested PCR fragment to the 1215 bp XhoI-MluI and the 10,873 bp fragment from p372MluI. The resultant plasmid was designated pHVIIIP$_{336.372}$, and was sequenced.

2. To obtain the porcine acidic region between residues 500 and 541 (human 700–740), the oligonucleotide A2B-700 5' number 15 and A2B-740 3' number 16 Table III were used in a PCR reaction of por 302 using Vent polymerase. Upon 25 cycles of amplification, the product obtained was digested with MluI, separated on an agarose gel and purified. The plasmid p700–740 was digested with MluI and the linear fragment was isolated and ligated to the MluI digested PCR fragment. The resultant plasmid was designated pHVIIIP 700–740, and was sequenced.

3. To obtain the porcine A2 domain from 138–541 (human 336–740), the oligonucleotide number 17 and 3' number 16 Table III were used in a PCR reaction of por 302 using Vent polymerase. Upon 25 cycles of amplification, the product obtained was digested with MluI, separated on an agarose gel and purified. The factor VIII chimera harboring 336–740 was constructed by ligation of the MluI digested PCR fragment to the XhoI-MluI fragment from p336 MluI and the 10,873 bp fragment from p372MluI. The resultant plasmid was designated pHVIIIP$_{336-740}$, and was sequenced.

4. To obtain the porcine A2 domain from 174–541 (human 372–740), the oligonucleotide 5' number 13 and 3' number 14 Table III were used in a PCR reaction of por 302 using Vent polymerase. Upon 25 cycles of amplification, the product obtained was digested with MluI, separated on an agarose gel and purified. Plasmid αA2 was digested with MluI, and the large fragment was isolated and ligated to MluI digested PCR fragment and the resultant plasmid was designated pHVIII$_{372-740}$, and was sequenced.

5. The KpnI-SpEI small fragment from plasmid pHVIIIP$_{332-372}$ was ligated to the large KpnI-SpEI fragment from pHVIIIP$_{700-740}$ and was designated pHVIIIP$_{336-372/700-740}$.

Plasmid DNAs were prepared by banding DNA in CsCl and used to transfect COS-1 cells. For co-transfection/co-expression experiments, 8 μg of each plasmid were transfected per tissue culture plate (P100). At 60 hr post transfection, conditioned media in the presence of 10% fetal calf serum was harvested and centrifuged to remove cellular debris. Immediately, factor VIII was assayed by its ability to clot factor VIII-deficient plasma (activated partial thromboplastin time, APTT) in both a one-stage and two-stage assay. Factor VIII activity was also measured in the Kabi Coatest Chromagenic assay. Cells were labeled with $^{35}$S-methionine, conditioned medium was harvested and immunoprecipitated with either monoclonal or polyclonal antibodies specific to factor VIII. Prior to separation by SDS-PAGE, half the immunoprecipitate was digested with thrombin. Factor VIII in the conditioned medium was also quantitated by SDS-PAGE and Western blotting. The amount of factor VIII present was measured by SDS-PAGE. The results obtained are set forth in Table V.

TABLE V

| CONSTRUCT | Kabi Coatest ACTIVITY mU/ml | % of Control |
|---|---|---|
| pHVIIIP$_{336-372}$ | 174[1] | 151 |
| pHVIIIP$_{700-740}$ | 105[1] | 91 |
| pHVIIIP$_{336-740}$ | 438[1] | 380 |
| pHVIIIP$_{372-740}$ | 198[1] | 171 |
| pHVIIIP$_{336-372/700-740}$ | 350[2] | 135 |

[1]human FVIII wild type control = 115
[2]human FVIII wild type control = 264

Thrombin treatment of the pHVIIIP$_{336-740}$ and pHVIIIP$_{372-740}$ hybrid FVIII molecules resulted in a 2–10 fold greater activation in coagulant activity compared to wild-type human recombinant FVIII. In addition, the pHVIIIP$_{372-740}$ activated hybrid protein retained activity under physiological pH for greater than 30 minutes, whereas wild-type human FVIII lost 95% of its coagulant activity after 10 minutes. These data demonstrate that the sequences responsible for increased stability of porcine factor VIII lie within the A2 domain and, more precisely, based on the above data, between residues 372–700.

EXAMPLE 4

PHARMACEUTICAL COMPOSITION AND USE OF HUMAN/PORCINE FACTOR VIII

A. Pharmaceutical Composition

The chimeric factor VIII-type procoagulant proteins of this invention can be formulated into pharmaceutically acceptable compositions with parenterally acceptable vehicles and excipients in accordance with procedures known in the art. The pharmaceutical compositions of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g., in sealed ampoules or vials.

Such pharmaceutical compositions may also contain pharmaceutically acceptable carriers, diluents, fillers, salts, buffers, stabilizers, and/or other materials well known in the art. The term "pharmaceutically acceptable" means a non-toxic material that does not interfere with the effectiveness of the biological activity of the active ingredient(s). The characteristics of the carrier or other material will depend on the route of administration.

The amount of chimeric factor VIII-type procoagulant proteins in the pharmaceutical composition of the present invention will depend upon the nature and severity of the condition being treated, and on the nature of prior treatments which the patient has undergone. Ultimately, the attending physician will decide the amount of chimeric factor VIII-type procoagulant protein with which to treat each individual patient. The duration of intravenous therapy similarly will vary, depending on the severity of the disease being treated and the condition and potential idiosyncratic response of each individual patient.

B. Method of Use

Pharmaceutical compositions containing the chimeric factor VIII-type procoagulant proteins of the present invention may be used to treat patients suffering from hemophilia caused by deficiency of factor VIII.

In practicing the method of treatment of this invention, a therapeutically effective amount of chimetic factor VIII-type procoagulant protein is administered to a mammal having a hemophiliac condition caused by factor VIII deficiency. The term "therapeutically effective amount" means the total amount of each active component of the method or composition that is sufficient to show a meaningful patient benefit, i.e., cessation of bleeding.

Administration of the chime fie factor VIII-type procoagulant proteins can be carried out in a variety of conventional ways. Intravenous administration to the patient is preferred. When administered by intravenous injection, the chimeric factor VIII-type procoagulant proteins of the invention will be in the form of pyrogen-free, parenterally acceptable aqueous solutions. A preferred pharmaceutical composition for intravenous injection should contain, in addition to the chimeric factor VIII-type procoagulant proteins, an isotonic vehicle such as sodium chloride injection, Ringer's injection, dextrose injection, dextrose and sodium chloride injection, lactated Ringer's injection, or other vehicle as known in the art. The pharmaceutical composition according to the present invention may also contain stabilizers, preservatives, buffers, anti-oxidants, or other additive known to those of skill in the art.

For cutaneous or subcutaneous injection, the chimeric factor VIII-type procoagulant protein of the invention will be in the form of pyrogen-free, parenterally acceptable aqueous solutions. The preparation of such parenterally acceptable protein solutions, having due regard to pH, isotonicity, stability, and the like, is within the skill in the art.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims be placed thereon. Accordingly, it is intended in the appended claims to cover all such equivalent variations which come within the scope of the invention as claimed.

What is claimed is:

1. A composition comprising a nucleic acid encoding factor VIII having factor VIII coagulant activity selected from the group consisiting of:
    (a) human domains A1, B, A3, C1; and porcine domain A2;
    (b) human domains B, A3, C1 and C2; and porcine domains A1 and A2;
    (c) human domains A1, A3, C1 and C2; and porcine A2; and
    (d) human domains A3, C1 and C2; and porcine domains A1 and A2.

2. A procaryotic or eucaryotic host cell transformed or transfected with a nucleic acid of claim 1.

3. The prokaryotic transformed host cell of claim 2 which is *E. coli* DH5 cells designated as por302 and corresponding to ATCC No: 69387.

4. A viral or circular nucleic acid plasmid comprising a nucleic acid of claim 1.

5. The viral or circular nucleic acid plasmid of claim 4 further comprising an expression control sequence operatively associated with said nucleic acid.

6. A method for the production of factor VIII comprising:
    growing, in culture, a host cell transformed or transfected with a nucleic acid of claim 1,
    isolating from said host cell and culture, the polypeptide product of the expression of said nucleic acid.

7. A method for the production of factor VIII comprising:
    disposing a nucleic acid of claim 1 in a cell free transcription and translation system; and
    isolating from said system the polypetide expression product of said nucleic acid.

8. The method of claim 6, wherein said factor VIII is human/porcine factor VIII.

9. A procaryotic or eucaryotic host cell transformed or transfected with nucleic acid selected from the group consisting of the nucleic acid of claim 1.

10. A viral or circular nucleic acid plasmid comprising a nucleic acid sequence selected from the group consisting of the nucleic acid of claim 1.

11. The viral or circular nucleic acid plasmid of claim 10 further comprising an expression control sequence operatively associated with said nucleic acid.

12. A method for the production of factor VIII activity comprising:

growing, in culture, a host cell transformed or transfected with a nucleic acid of claim 1 and isolating from said host cell, or culture, the polypeptide product of the expression of said nucleic acid.

13. A method for the production of factor VIII activity comprising:

disposing a nucleic acid of claim 1 in a cell free transcription and translation system; and isolating from said system the polypeptide expression product of said nucleic acid.

14. The method of claim 12 or 13, wherein said factor VIII activity is human/porcine factor VIII activity.

15. A composition comprising a nucleic acid encoding a protein having factor VIII coagulant activity and factor VIII amino acids corresponding to:

human 1–335 and 373–2332 of SEQ ID NO. 2 and porcine 138–174 of SEQ ID NO. 4.

16. The nucleic acid of claim 15 encoding amino acids corresponding to:

human 1–335 and 741–2332 of SEQ ID NO. 2 and porcine 138–541 of SEQ ID NO. 4.

17. A composition comprising a nucleic acid encoding a protein having factor VII coagulant activity and Factor VII amino acids corresponding to:

human 1–371 and 741–2332 of SEQ ID NO. 2 and porcine 174–541 of SEQ ID NO. 4.

18. A composition comprising a nucleic acid encoding a protein having factor VIII coagulant activity and Factor VII amino acids corresponding to:

human 1–699 and 741–2332 of SEQ ID NO. 2 and porcine 501–541of SEQ ID NO. 4.

19. A composition comprising a nucleic acid encoding a protein having factor VIII coagulant activity and Factor VII amino acids corresponding to:

human 1–335,373–699, and 74114 2332 of SEQ ID NO. 2 and porcine 138–174 and 501–541 of SEQ ID NO. 4.

20. A method for the production of porcine factor VIII activity comprising:

growing, in culture, a host cell transformed with a nucleic acid of SEQ ID No:3; and isolating from said host cell, or culture, the polypeptide product of the expression of said nucleic acid.

21. A method for the production of porcine factor VIII activity comprising:

disposing all or part of a nucleic acid of SEQ ID NO:3 in a cell free transcription and translation system; and isolating from said system the polypeptide product of the expression of said nucleic acid.

22. A factor VIII expression product of the in vitro or in vivo expression of a nucleic acid of claim 1.

23. An amino acid sequence of SEQ ID NO:4.

24. A composition comprising a nucleic acid encoding factor VIII having factor VIII coagulant activity comprising two domains substantially duplicative of a sequence of amino acids comprising a domain selected from (a) and a domain selected from (b), wherein:

(a) is one or more members selected from the group consisting of human domains A1, A2, B, A3, C1 and C2, and (b) is one or more members selected from the group consisting of porcine domains A1, A2, B, A3, C1, and C2.

25. A method for treating hemophilia comprising the step of administering the factor VIII expression product of claim 22.

26. A pharmaceutical composition comprising the factor VIII expression product of claim 22.

* * * * *

UNITED STATES PATENT AND TRADEMARK OFFICE
CERTIFICATE OF CORRECTION

PATENT NO.   :   5,563,045

DATED        :   October 8, 1996

INVENTORS    :   Pittman, et al.

It is certified that error appears in the above-identified patent and that said Letters Patent is hereby corrected as shown below:

At column 12, line 10, replace "reseels" with --resects--.

At column 12, line 13, replace "VHI" with --VIII--.

At Table III, No. 7, FVIII 336, second line of sequence, delete "AA <u>ACG</u> <u>CGT</u> ATC AAA AAT" and replace with --AA <u>ACG</u> <u>CGT</u> ATG AAA AAT--.

At column 14, line 24, replace "VHI" with --VIII--.

At column 14, line 58, replace "A1" with --A2--.

At column 15, line 43, replace "pHVIIIP$_{336.372'}$" with --pHVIIIP$_{336-372}$--.

At column 15, line 53, replace "pHVIIIP 700-740," with --pHVIIIP$_{700-740}$--.

At column 16, line 4, replace "aA2" with --ΔA2--.

At column 16, lines 41/42, replace "control=" with --control ≡ --.

At column 17, line 33, replace "chimetic" with --chimeric--.

At column 18, line 4, replace "chime fie" with --chimeric--.

IN THE CLAIMS:

At column 64, line 4, replace "74114-2332" with --741-2332--.

Signed and Sealed this

Twenty-fourth Day of June, 1997

*Attest:*

BRUCE LEHMAN

*Attesting Officer*   *Commissioner of Patents and Trademarks*